US007559907B2

(12) United States Patent
Krempel et al.

(10) Patent No.: US 7,559,907 B2
(45) Date of Patent: Jul. 14, 2009

(54) TEMPERATURE-CONTROLLABLE DEVICE

(75) Inventors: Benjamin J. Krempel, San Francisco, CA (US); Eric C. Selvik, Menlo Park, CA (US); Eric J. Altman, San Francisco, CA (US); Matt R. Buchter, San Francisco, CA (US); Alfredo T. Del Rio, San Francisco, CA (US); Robert T. Dennis, San Francisco, CA (US); Mark V. Martin, San Francisco, CA (US)

(73) Assignee: Aqueduct Medical, Inc., San Francisco, CA (US)

( * ) Notice: Subject to any disclaimer, the term of this patent is extended or adjusted under 35 U.S.C. 154(b) by 400 days.

(21) Appl. No.: 11/064,546

(22) Filed: Feb. 23, 2005

(65) Prior Publication Data
US 2005/0187502 A1    Aug. 25, 2005

Related U.S. Application Data

(60) Provisional application No. 60/546,903, filed on Feb. 23, 2004.

(51) Int. Cl.
*A61F 5/00* (2006.01)
(52) U.S. Cl. ............. 602/6; 602/5; 602/12; 602/14
(58) Field of Classification Search .......... 602/2, 602/5, 13, 14; 606/191, 192, 96, 108–110, 606/112, 114; 128/857, 858, 847; 2/206; 604/291
See application file for complete search history.

(56) References Cited

U.S. PATENT DOCUMENTS 2,252,423 A * 8/1941 Baddour ............... 219/527

(Continued)

FOREIGN PATENT DOCUMENTS

WO    WO-95/10251 A1    4/1995

(Continued)

OTHER PUBLICATIONS

Buist, R.J. et al. (1996). "Theoretical Analysis of Thermoelectric Cooling Performance Enhancement Via Thermal and Electrical Pulsing," *15 International Conference on Thermoelectrics*, pp. 234-237.

(Continued)

*Primary Examiner*—Kim M Lewis
(74) *Attorney, Agent, or Firm*—Lumen Patent Firm

(57) ABSTRACT

Described herein are temperature-controllable devices, and methods for using them. In some variations, the devices comprise a fluid passageway region, which is configured to allow a fluid to flow therethrough, and a splint. The splint may be moldable to at least a portion of a subject's anatomy, e.g., a nose. In other variations, the devices comprise a fluid passageway region configured to allow a fluid to flow therethrough, and an absorbent pad. In some variations, the devices comprise three layers, in which two of the layers form a fluid passageway region and the third layer forms a pocket or pouch. In this way, the pouch may be configured to receive at least one splint therein, e.g., in order to provide support to an injured area such as a nose. Methods for using the devices to treat an injured area are also described. Kits are also described.

26 Claims, 19 Drawing Sheets

U.S. PATENT DOCUMENTS

| | | | |
|---|---|---|---|
| 2,477,883 A * | 8/1949 | Lefohn | 607/109 |
| 2,991,627 A | 7/1961 | Suits | |
| 3,085,405 A | 4/1963 | Frantti | |
| 3,136,577 A | 6/1964 | Richard | |
| 3,173,419 A * | 3/1965 | Dubilier et al. | 607/109 |
| 3,606,890 A * | 9/1971 | Gilbert | 607/104 |
| 3,908,655 A | 9/1975 | Lund | |
| 4,108,146 A | 8/1978 | Golden | |
| 4,243,041 A | 1/1981 | Paul | |
| 4,274,402 A | 6/1981 | Shippert | |
| 4,459,468 A | 7/1984 | Bailey | |
| 4,470,263 A | 9/1984 | Lehovec et al. | |
| 4,483,021 A | 11/1984 | McCall | |
| 4,523,594 A | 6/1985 | Kuznetz | |
| 4,528,540 A | 7/1985 | Stiekel et al. | |
| 4,614,189 A * | 9/1986 | MacKenzie | 607/109 |
| 4,677,970 A | 7/1987 | Green et al. | |
| 4,685,453 A * | 8/1987 | Guignard et al. | 602/7 |
| 4,741,338 A | 5/1988 | Miyamae | |
| 4,844,072 A | 7/1989 | French et al. | |
| 4,846,176 A | 7/1989 | Golden | |
| 4,930,317 A | 6/1990 | Klein | |
| 4,962,761 A | 10/1990 | Golden | |
| 5,022,389 A | 6/1991 | Brennan | |
| 5,072,875 A | 12/1991 | Zacoi | |
| 5,097,829 A | 3/1992 | Quisenberry | |
| 5,169,384 A * | 12/1992 | Bosniak et al. | 604/20 |
| 5,190,032 A | 3/1993 | Zacoi | |
| 5,241,951 A | 9/1993 | Mason et al. | |
| 5,344,436 A | 9/1994 | Fontenot et al. | |
| 5,562,604 A | 10/1996 | Yablon et al. | |
| 5,566,062 A | 10/1996 | Quisenberry et al. | |
| 5,628,772 A * | 5/1997 | Russell | 607/109 |
| 5,643,336 A | 7/1997 | Lopez-Claros | |
| 5,682,748 A | 11/1997 | DeVilbiss et al. | |
| 5,711,155 A | 1/1998 | DeVilbiss et al. | |
| 5,800,490 A | 9/1998 | Patz et al. | |
| 5,806,335 A | 9/1998 | Herbert et al. | |
| 5,813,233 A | 9/1998 | Okuda et al. | |
| 5,817,039 A | 10/1998 | Raunig | |
| 5,871,526 A | 2/1999 | Gibbs et al. | |
| 5,895,418 A | 4/1999 | Saringer | |
| 5,947,123 A | 9/1999 | Shippert | |
| 5,948,012 A | 9/1999 | Mahaffey et al. | |
| 6,006,524 A | 12/1999 | Park | |
| 6,023,932 A | 2/2000 | Johnston | |
| 6,074,414 A | 6/2000 | Haas et al. | |
| 6,117,164 A | 9/2000 | Gildersleeve et al. | |
| 6,125,636 A | 10/2000 | Taylor et al. | |
| 6,126,683 A * | 10/2000 | Momtaheni | 607/109 |
| 6,152,952 A | 11/2000 | Owens | |
| 6,232,543 B1 | 5/2001 | Nagata | |
| 6,248,125 B1 | 6/2001 | Helming | |
| 6,295,819 B1 | 10/2001 | Mathiprakasam et al. | |
| 6,320,095 B1 | 11/2001 | Wall | |
| 6,352,550 B1 | 3/2002 | Gildersleeve et al. | |
| 6,416,534 B1 | 7/2002 | Montagnino et al. | |
| 6,562,060 B1 | 5/2003 | Momtaheni | |
| 6,583,710 B2 | 6/2003 | Hayashi et al. | |
| 6,648,909 B2 | 11/2003 | Helming | |
| 6,758,215 B2 * | 7/2004 | Begum | 128/203.29 |
| 6,786,880 B2 | 9/2004 | Wall | |
| 2001/0018605 A1 | 8/2001 | Helming | |
| 2001/0039439 A1 * | 11/2001 | Elkins et al. | 607/104 |
| 2002/0026226 A1 | 2/2002 | Ein | |
| 2002/0052566 A1 | 5/2002 | Sequeira | |
| 2002/0107491 A1 | 8/2002 | Wall | |
| 2003/0118074 A1 | 6/2003 | Seki et al. | |
| 2004/0068309 A1 | 4/2004 | Edelman | |
| 2004/0138598 A1 | 7/2004 | Kortuem et al. | |
| 2004/0167456 A1 | 8/2004 | Kingsford et al. | |
| 2004/0194195 A1 * | 10/2004 | Palmer et al. | 2/424 |

FOREIGN PATENT DOCUMENTS

| | | |
|---|---|---|
| WO | WO-2005/007060 A2 | 1/2005 |
| WO | WO-2005/007060 A3 | 1/2005 |

OTHER PUBLICATIONS

Buist, R.J. et al. (Aug. 10, 1994). "Thermoelectric Heat Sink Modeling and Optimization," *Thirteenth International Conference on Thermoelectrics AIP Conference Proceedings*, Kansas City, MO, 316:135-138.

Burke, E.J. et al. (Nov. 14-19, 1982). "A Thermoelectric Cooling/Heating System for a Hospital Therapy Pad," *The American Society of Mechanical Engineers*, Phoenix, AZ, pp. 80-83.

Invitation to Pay Additional Fees mailed Jun. 2, 2005 for International Patent Application No. PCT/US2005/006027, 8 pages.

Nagy, M.J. et al. (Aug. 10, 1994). "Effect of Heat Sink Design on Thermoelectric Cooling Performance," *Thirteenth International Conference on Thermoelectrics AIP Conference Proceedings*, Kansas City, MO, 316(1):147-149.

Palacios, R. et al. (Sep. 1998). "Electrical Properties of Commercial Thermoelectric Modules," *Fourth European Workshop on Thermoelectrics*, Madrid, Spain, pp. 159-162.

Ritzer, T.M. et al. (Aug. 10, 2004). "Economic Optimization of Heat Sink Design," *Thirteenth International Conference on Thermoelectrics AIP Conference Proceedings*, Kansas City, MO, 316:177-180.

Streitwieser, G.D. et al. (Mar. 16-18, 1988). "An Electronic Temperature Controller for Thermoelectrics with Variable Heat Sink Resistance," *Seventh International Conference of Thermoelectric Energy Conversion*, Arlington, TX, pp. 110-114.

* cited by examiner

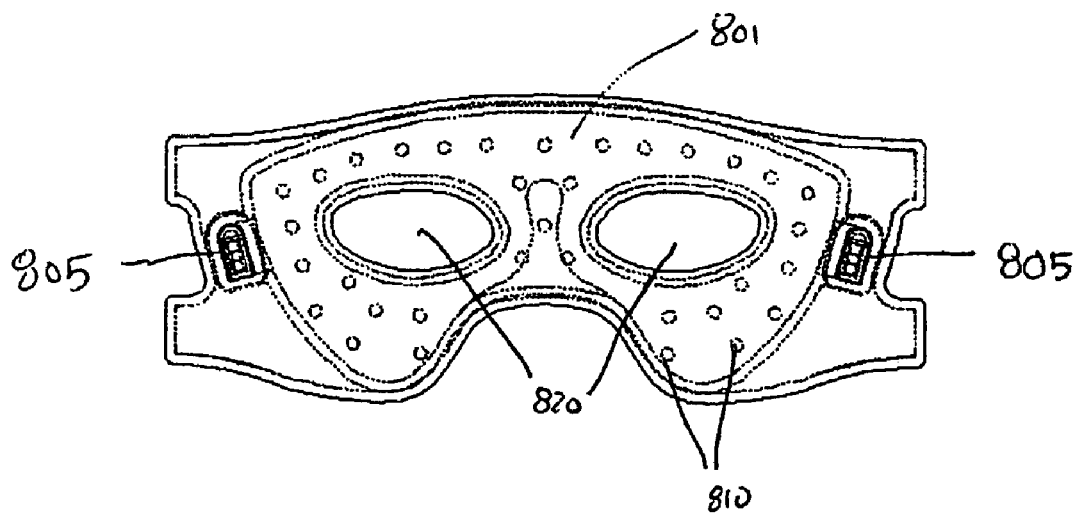
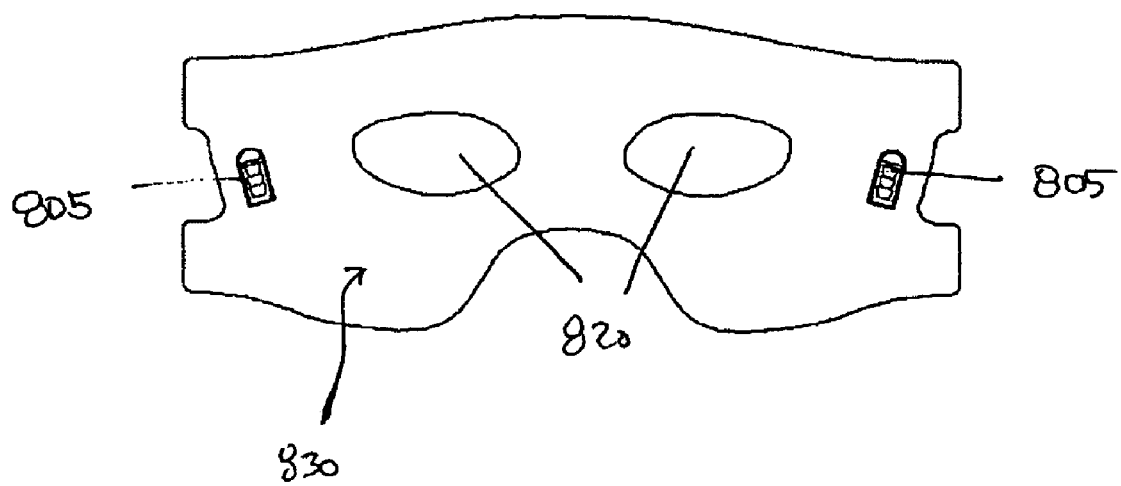

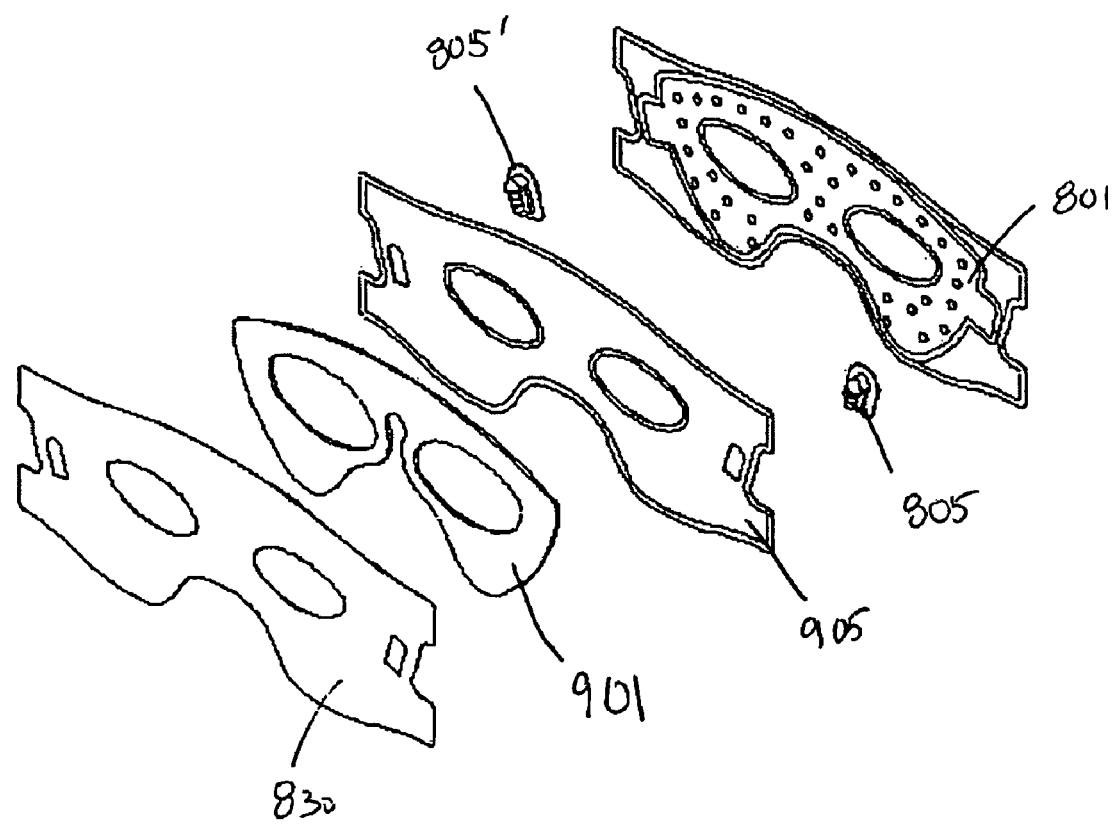

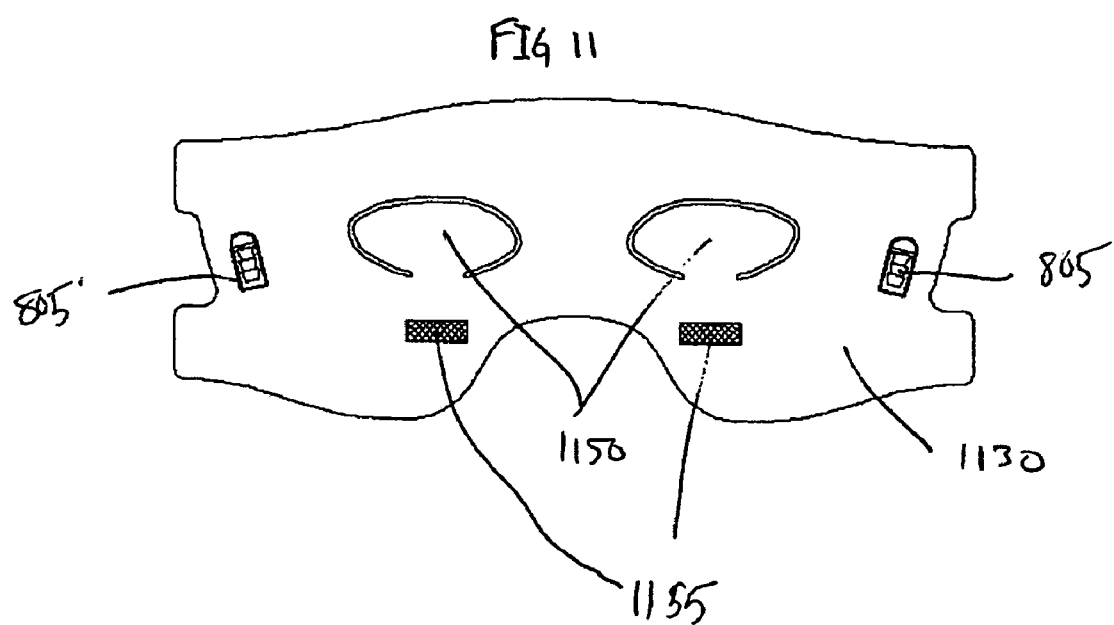

FIG. 14A
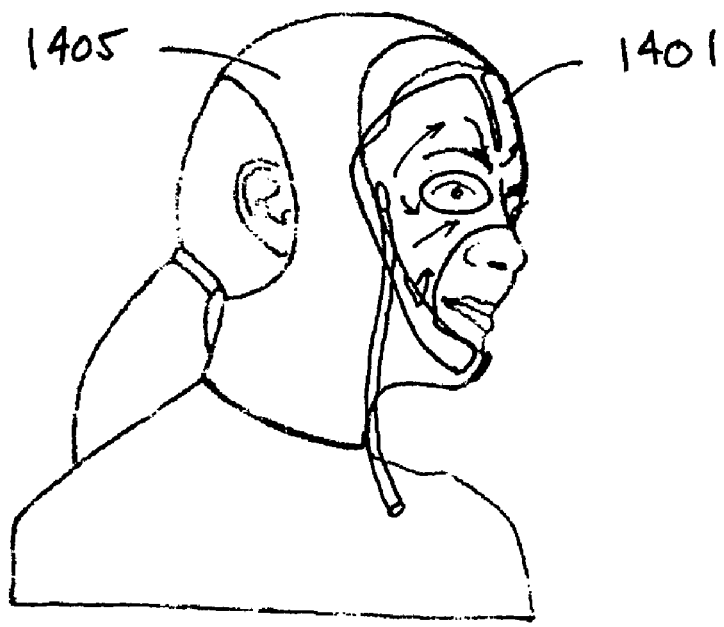
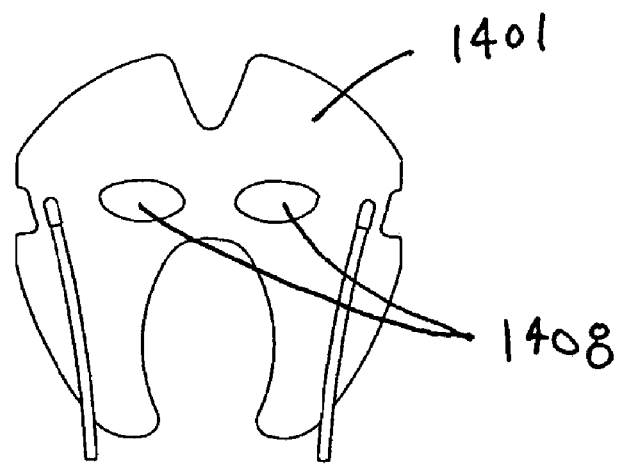
FIG. 14B

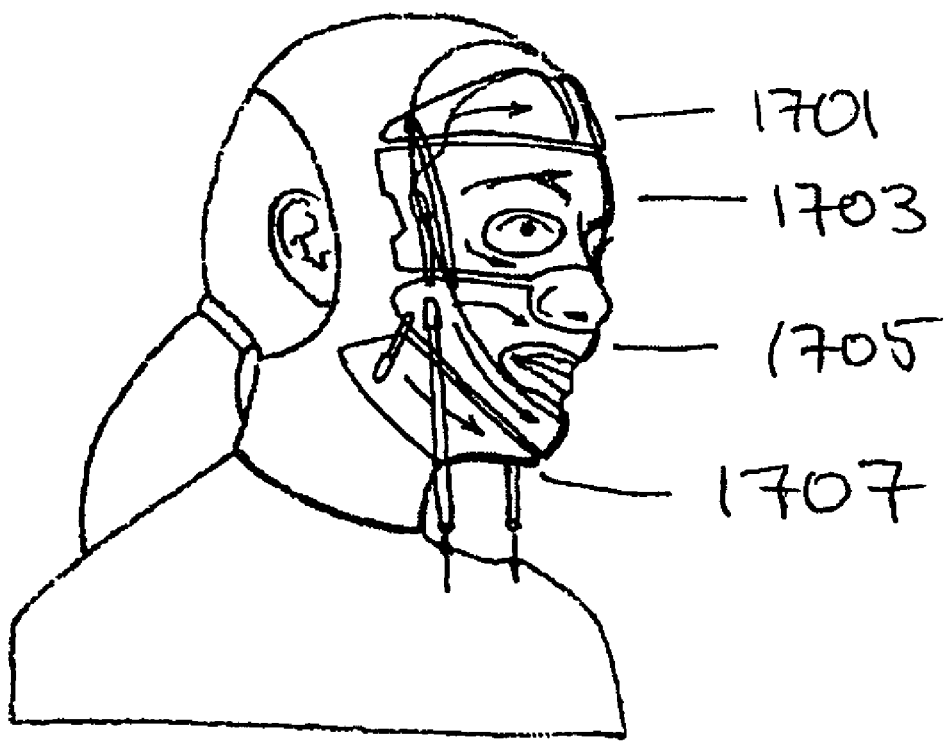

TEMPERATURE-CONTROLLABLE DEVICE

CROSS-REFERENCE TO RELATED APPLICATIONS

This application claims priority to U.S. Provisional Application No. 60/546,903, entitled "Temperature-Controllable Device" (filed Feb. 23, 2004).

FIELD

The present invention relates to the field of temperature-controllable devices and methods for using them. More particularly, the devices and methods described herein relate to the field of post-surgery (or injury) recovery.

BACKGROUND

Surgery and injury typically generate swelling and bruising about the injured area. Currently, it is common practice to treat this injured area with ice or other forms of cold therapy. Indeed, cooling an injured area is thought to decrease blood flow, edema, hemorrhaging, inflammation, muscle spasms, and pain. In addition, cooling an injured area often serves to provide temporary relief to a subject. There are a number of ways currently used to cool down an injured area. For example, freezer-based devices such as ice and gel-packs may be used. Continuous cold therapy devices may also be used, and may have advantages over freezer-based devices. Continuous cold therapy devices typically consist of a thin pad that is placed on the affected body area through which cold water is circulated. Some of these solutions are ice-based and some of them employ refrigeration means to produce the temperature change. However, both freezer-based solutions and continuous cold therapy devices may be limited by shortcomings reflected in their effectiveness and popularity, especially when used after plastic surgery or for application on the face.

Freezer-based devices such as ice packs and gel packs may have a number of characteristics which limit their effectiveness. For example, freezer-based devices are typically held at temperatures below freezing, which may be too cold for continuous use on the skin. The cold temperature may cause frostbite and in extreme cases can result in dermal necrosis. To reduce this risk, it is recommended that ice is applied 20 minutes on and 20 minutes off. Another shortcoming is that it may be difficult to for the devices to conform to complex shapes such as those found on the knee, hand, face or shoulder. The thickness of the device may limit the flexibility and the ability of the pad to conform to affected area. If the thickness is reduced, this typically reduces the ability of the pad to absorb heat, which limits the time that the device will remain in a therapeutic range. Freezer-based devices may also be difficult to secure comfortably on the body due to their size and weight. Thus, the effective use of freezer-based devices may require constant patient interaction in order for the devices to be used effectively, thereby limiting the activities that can be done while applying the therapy. For example, it may be difficult to sleep and perform other activities while ensuring that a uniform, constant therapy is being applied.

Continuous cold therapy devices may improve upon freezer-based devices by automating the cooling process. The systems may consist of a therapeutic pad that is placed on the body and a cooling unit which circulates cold water though the pad. Some versions of these devices use ice to absorb the heat and provide the cooling. Fully electric systems using thermoelectric modules are also available.

Ice-based cooling devices may have significantly improved performance compared to freezer-based solutions. However, because they use ice, ice-based cooling devices must be constantly emptied and refilled with ice. The device can be heavy, and the re-filling process can be difficult, especially for someone who has an injury or is recovering from surgery. Also, because the devices may consume more ice than is readily available from a home freezer, a user may have to purchase ice to use the ice-based cooling devices. The devices may also be difficult to maintain at a desired therapeutic temperature, and the ice bath may pose an increased risk of frostbite and tissue damage if the low-end temperature is not properly regulated. As the ice melts, the temperature may also rise, which limits the control and repeatability of the temperature management and the effectiveness of the therapy. A thermoelectric, continuous cold therapy device may solve some of these shortcomings.

A thermoelectric device may use electricity to dissipate body heat and to cool circulating water. The temperature of a thermoelectric device can be easily regulated by electronic or mechanical means and offers a safe, repeatable therapy for patient recovery. Historically, thermoelectric units have been too expensive to be popular home appliances and have mostly been limited to hospital and clinic applications.

Ice-based continuous cold therapy devices and pads have achieved most of their commercial success in the field of orthopedic recovery. For application in other disciplines such as cosmetic surgery, the devices may have several shortcomings. Many cold therapy pads may not provide direct contact to an injured area. Furthermore, many cold therapy devices may not conform closely to an injured area. This concern is of particular importance in areas such as cosmetic surgery where the injured body part, or parts, are typically irregularly shaped (e.g., the eyes, nose, neck, breasts, ears, etc.). In addition, it may be particularly important, especially on the face, to reduce the wrinkling of the pad and other points of pressure concentration that may be uncomfortable to users. The comfort demands for the face are much higher than they are for less sensitive parts of the body. The temperature range of acceptable therapy temperatures may be much stricter for facial applications than for other cold-therapy applications. The risk of frostbite, dermal necrosis and other tissue damage should be minimized or eliminated to assure patients and doctors that the therapy is safe.

In many cosmetic surgery procedures, it can be of great importance to stabilize the injured area (e.g., to maintain facial bones in place, secure skin flaps). For example, nose splints have been developed to maintain pressure on precise areas of the nose to control swelling or distortion of the nose, which can disrupt the normal healing process, and potentially lead to less than desirable cosmetic results. Splints for these purposes have been developed from metals, plasters and the like.

Accordingly, it would be desirable to have improved devices for application to, and treatment of, an injured area. Similarly, it would be desirable to have flexible, moldable and settable devices capable of cooling an injured area, yet that have sufficient structure and strength to provide adequate pressure and stability to the injured area. It would also be desirable to have devices that allow for continuous temperature control and adjustment. In a like fashion, devices that can be applied to an injured area immediately after surgery, and be continuously worn and used at home, would be desirable.

SUMMARY

Described herein are temperature-controllable devices, and methods for using them. In some variations, the temperature-controllable devices comprise a fluid passageway region, which is configured to allow a fluid to flow therethrough, and a splint. The splint is moldable to at least a portion of a subject's anatomy, e.g., a subject's nose, and in some variations, the fluid passageway region is configured to contact at least a portion of a subject's anatomy.

One variation of the temperature-controllable device includes a pliable fluid passageway region for allowing fluid to flow therethrough and a splint configured to be re-formable, wherein the splint is moldable to at least a portion of a subject's anatomy.

The splint may connect to the fluid passageway region. In some variations, the splint is releasably connected to the fluid passageway. For example, the splint may be releasably connected by a fastener selected from the group consisting of hook and loop fasteners, adhesives, snaps, rivets, buttons, zippers, magnets, and friction fittings. The splint may support a portion of the fluid passageway region, and may apply pressure to the fluid passageway region. The splint may also include a pressure-adjustable bladder. In some variations, the splint comprises a thermoplastic material. In some variations, the splint is made at least in part from a material selected from the group consisting of aluminum, stainless steel, tin, plastic, an alloy, a wax, rubber, and mixtures thereof. The splint may be made from a material having a high thermal conductivity, or a material having a low thermal conductivity. The splint may have at least one perforation therethrough, and may be deformable along a pattern of perforations therethrough. In some variations, at least a region of the splint (e.g., a surface) has a texture selected from the group consisting of smooth, dimpled, creased, ridged, corrugated, crimped, crinkled, furrowed, knitted, puckered, wrinkled, and combinations thereof. The splint may also be configured to include a frame. The splint may have multiple pieces. The splint may also be at least partly enclosed within the fluid passageway region. In some variations, the temperature-controllable device includes multiple splints.

The fluid passageway region may have at least a portion that has a high thermal conductivity, and the portion having a high thermal conductivity may contact at least a portion of a subject's anatomy. In some variations, the region of high thermal conductivity has a textured surface, selected from the group consisting of smooth, dimpled, creased, ridged, corrugated, crimped, crinkled, furrowed, knitted, puckered, wrinkled, pleated and combinations thereof.

In some variations, the fluid passageway region is made at least in part from a material selected from the group consisting of vinyl, polyvinyl chloride, rubber, urethane, polyurethane, neoprene, silicone, and mixtures thereof. The fluid passageway may be configured to permit pulsatile fluid flow. The fluid passageway may include interconnected regions, and fluid may be blocked from selectable regions. A temperature-controllable device may include valves (or obstructions) configured to selectively block fluid flow into, and out of, selected regions. The valves may be of a type selected from the group consisting of a snap, a button, a rivet, a zipper, a clamp, a magnet, an adhesive, and combinations thereof. In some variations, individual regions of the interconnected regions may be configured to permit pulsatile fluid flow. Interconnected regions may be arranged so as to minimize pressure drop of fluid moving through the fluid passageway. In some variations, the fluid passageway may have a non-uniform thickness configured to correspond to a region of a subject's anatomy.

A temperature-controllable device may include a splint that is moldable to a subject's face. The temperature-controllable device may also include eye flaps that may close to cover a subject's eyes. In some variations, the fluid passageway extends into the eye flaps. The eye flaps may be secured in an open or closed position. A temperature-controllable device may also include a splint that is moldable to a subject's nose.

In some variations, the temperature-controllable device includes a fluid within the fluid passageway region (e.g., water). The fluid may be a liquid having a high thermal conductivity. The device may also include an adhesive. In some variations, the adhesive is configured to contact at least a portion of the subject's skin and temporarily adhere the device thereto. In some variations, the adhesive is configured to contact at least a portion of a subject's garment, and adhere the device thereto.

The temperature-controllable device may also include a sterile portion, wherein the sterile portion is configured to contact at least a portion of the subject's skin. The sterile portion may be made (at least in part) from a sterile material selected from the group consisting of gauze, cotton, paper, plastic, polyurethane, silicone, polypropylene, and mixtures thereof.

In some variations, the temperature-controllable device includes an insulating outer portion, wherein the insulating outer portion is configured to provide thermal insulation between the device and the ambient environment. The temperature-controllable device may also include an inlet and an outlet, wherein both the inlet and the outlet are configured to attach to a fluid supply unit and to the fluid passageway region. The inlet and outlet may have flanged fittings. The inlet and the outlet may comprise quick-release attachments.

The temperature-controllable device may include an active agent within the fluid passageway. The active agent may be a compound selected from the group consisting of an antibacterial, an antifungal, an antimicrobial, a lubricant, an anticorrosive, a perfume, a dye, an antifreeze, an antimolding agent, and mixtures thereof. The active agent may be coated on the passageway walls, impregnated within the passageway walls, free-floating within the passageway, or the like.

The temperature-controllable device may be configured for a single use (e.g., disposable). The device (or portions of the device) may be washable. The device may include a pad configured to contact a portion of a subject's anatomy. The pad may be an absorbent pad. The pad may be connected to at least a portion of the fluid passageway. For example, the pad may be removeably connected to at least a portion of the fluid passageway. The pad may be connected to at least a portion of the fluid passageway by an adhesive. A pad used with the device may be configured for a single use. The pad may also include a sanitary barrier between the absorbent pad and at least a portion of the rest of the device. The pad may also be textured.

In some variations of the temperature-controllable device, the device includes an active agent. For example, the active agent may be selected from the group consisting of a cream, a petroleum-based product, a moisturizer, a surfactant, a disinfectant, an alcohol-based product, a cosmetic, a vitamin, an acid, a base, a pharmaceutical, or an anesthetic. The device may also include a pad for holding the active agent, which may include a removable protective cover.

The temperature-controllable device may also include a support structure for securing the device to a portion of a subject's anatomy. The support structure may be a headgear made from a formable material, a strap (e.g., a neckstrap), or a frame. The device may also include an attachment surface for attaching a support structure to the device. The support structure may attach to the attachment surface by a hook and loop fastener or the like. A strap may be used to secure the device to a subject, and may be configured to secure the device to a subject's garment. The strap may also be adjustable and/or elastic. In some variations, the strap is configured as a neckstrap.

The temperature-controllable device may also include an insulator mask adjacent to the fluid passageway region for selectively exposing a portion of the fluid passageway region to a subject.

Also described herein are methods of treating a portion of a subject's anatomy. A subject may be treated with the temperature-controllable device by applying the temperature-controllable device to a portion of the subject's anatomy in need of treatment, and controlling the temperature of the device so as to provide a therapeutic benefit.

Trays for molding a thermoplastic splint configured to be re-formable are also described. The tray may include a fluid bath region for holding a fluid and a temperature-controllable device, wherein the splint of the temperature-controllable device comprises a thermoplastic material. The tray may also include a temperature regulator for regulating the temperature of a fluid within the fluid bath at a temperature adequate to mold the thermoplastic material. In some variations, the tray includes an indicator for indicating when the temperature of a fluid within the fluid bath is adequate to mold the thermoplastic material. The tray may also include a fill line. The tray may also include a holder for holding at least the splint portion of the temperature-controllable device in the tray. For example, the holder may keep the splint submerged beneath a fluid in the tray. The holder may comprise any holder appropriate for securing a device having a splint, or appropriate for securing just a splint.

Kits may be provided for treating a portion of a subject's anatomy with a temperature-controllable device. The kits may include a temperature-controllable device and instructions for using the temperature-controllable device. The kits may also include a fluid source unit for supplying temperature-regulated fluid to the temperature-controllable device. The kits may also include straps, for securing the device to the user.

Also described herein are temperature-controllable devices having three or more layers. The temperature-controllable devices may include a fluid passageway region formed by a first layer and a second layer for allowing fluid to flow therethrough, and a third layer at least partly attached to the second layer, wherein the third layer and the second layer are configured to form a pocket. In some variations, the pocket is configured to hold a splint. The pocket may be sealed or be sealable. The pocket may also act as an insulating layer.

Temperature-controllable devices may be configured as periorbital masks that may fit over a subject's face (e.g., the periorbital region). These devices may have a pliable fluid passageway region for allowing fluid to flow therethrough, wherein the fluid passageway region comprises an inlet and an outlet port for connection to a thermally-regulated fluid source, and a splint, wherein the splint comprises a moldable and settable thermoplastic material for conforming to at least a portion of a subject's face. The periorbital masks may also include an attachment region for connecting to at least one strap for securing the device to a subject's face.

Also described herein are temperature-controllable devices having a fluid passageway region for allowing fluid to flow therethrough, an absorbent pad, and a holdfast for securing the absorbent pad to the fluid passageway region. A temperature-controllable device may also comprise a fluid passageway region for allowing fluid to flow therethrough and an active agent-releasing surface in thermal contact therewith. In some variations, the temperature-controllable devices comprise a fluid passageway region for allowing fluid to flow therethrough and a strap for supporting at least a portion of the weight of the device that does not attach to the device or to the region of the subject's anatomy being treated by the device.

BRIEF DESCRIPTION OF THE DRAWINGS

FIGS. 8A and 8B show one variation of a temperature-controllable device configured as a periorbital mask. FIG. 8A shows the contact facing side and FIG. 8B shows the outer surface.

FIG. 9 shows an exploded view of the periorbital mask of FIGS. 8A and 8B.

FIG. 11 shows one variation of a temperature-controllable device configured as a periorbital mask.

FIGS. 14A and 14B show one variation of a temperature-controllable device configured as a full face mask.

FIG. 17 shows four temperature-controllable devices connected together.

DETAILED DESCRIPTION

Figure 1A:
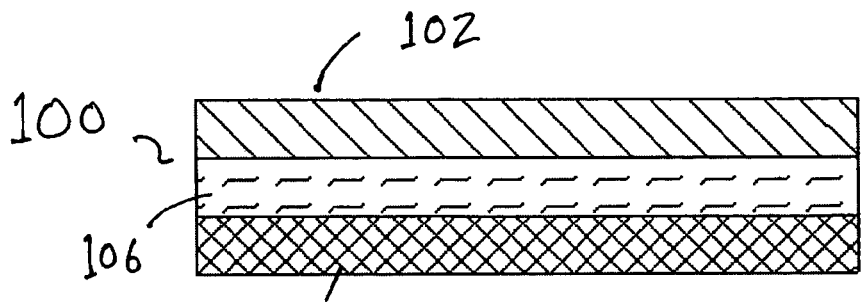
FIGS. 1A-1E depict cross-sectional views of illustrative devices described herein.

Described herein are temperature-controllable devices, and methods for using them. These devices may be made in such a way that they are useful in treating, or providing a therapeutic benefit, to a portion of the anatomy. For example, these devices may be configured so that they are useful in aiding the healing process after surgery or injury. Typically, surgery or injury results in swelling, bruising, and pain about the injured area. It has been well documented that direct application of ice or cold therapy to the injured area helps to reduce the swelling, bruising, and pain associated therewith.

In general, temperature-controllable devices may comprise a pliable fluid passageway region for allowing fluid to flow therethrough, and a splint configured to be re-formable that may be moldable to a portion of a user's anatomy. In some variations, the temperature-controllable device may comprise a fluid passageway region and an absorbent pad. In some variations, the temperature-controllable device may comprise three or more layers. A first and second layer may form a fluid passageway for allowing fluid to flow therethrough, and a third layer may be at least partly attached to the first or second layer to form a pocket.

A. Fluid Passageway Region

A fluid passageway may comprise a region of the temperature-controllable device in which fluid may flow to regulate the temperature of the temperature-controllable device. The fluid passageway region ("fluid passageway") may be enclosed, and may include a fluid inlet and a fluid outlet. In some variations, the path of fluid traveling through the fluid passageway may be predetermined (e.g., by the shape or design of the fluid passageway) or fluid may be allowed to flow and mix within the fluid passageway. In some variations, the fluid passageway may comprise individual channels or a chamber.

The fluid passageway may comprise walls or sides preventing substantial leakage of fluid from the fluid passageway. The walls or sides of the fluid passageway may be made of any appropriate material allowing fluid to flow through the passageway. In some variations, the fluid does not leak from the fluid passageway. For example, the walls may be made of a waterproof (or water resistant material) such as a polymer (e.g., plastics), including vinyl, polyvinyl chloride, rubber, urethane, polyurethane, neoprene, silicone, and mixtures thereof. The fluid passageway may also include internal supports (e.g., spacers, columns, etc.) to maintain the open dimensions of the fluid passageway region (even when outside pressure is applied to the fluid passageway).

In some variations, the fluid passageway comprises a pliable fluid passageway. Thus, the fluid passageway may be configured to allow the passageway to flex, or bend, to at least some degree, without substantially inhibiting the passage of fluid through the fluid passageway. The shape of the fluid passageway may be selected so that the bending of the fluid passageway region does not substantially inhibit the flow of fluid. Furthermore, the fluid passageway may be of a thickness so that the fluid passageway permits some amount of pliability.

The fluid passageway may have any appropriate structure permitting the flow of fluid therein. In some variations, the fluid passageway may comprise a tubular structure. For example, the fluid passageway may include at least a region that is tubular in structure. Thus, the fluid passageway may be a long tube having an inlet at one end (e.g., a proximal end), and an outlet at another end (e.g., a distal end). The fluid passageway may be a bifurcated (e.g., interconnected) set of tubes which may divide into multiple tubes that may define separate or joined passages. In some variations, these passages may recombine.

The fluid passageway may also be formed as a large chamber. The chamber of the fluid passageway may have an inlet and an outlet for the inflow and outflow of fluid. In some variations, the fluid passageway is configured as a chamber permitting many different flow pathways. The fluid passageway may allow mixing of the fluid flowing within the fluid passageway. The fluid passageway may be constructed so that it flows between two substantially parallel surfaces (e.g., layers), that may be connected. For example, the fluid passageway may be defined by two layers that are connected at their edges, and also at various points in between.

The fluid passageway may also include any number of interconnected fluid chambers or interconnected regions. In some variations, the fluid passageway may comprise chambers of different sides and dimensions. Thus, flow through the fluid passageway may be controlled, in part, by the dimensions of interconnected regions of the fluid passageway. Interconnected regions of the fluid passageway may be connected in any appropriate manner to permit or regulate the flow of fluid within the fluid passageway, or a portion of the fluid passageway. For example, interconnected regions of the fluid passageway may have openings (e.g., an inlet and outlet) connecting them to other regions of the fluid passageway that permit them to be selectively opened or closed, or partially opened or closed, thereby controlling the fluid flow through regions of the temperature-regulated device. Thus, fluid flow through the fluid passageway (including regions or chambers of the fluid passageway) may be regulated by valves configured to selectively block flow of fluid into and out of selected regions of the fluid passageway. Any appropriate valve may be used to regulate the flow of a fluid within the fluid passageway, or a region of the fluid passageway, for example, snaps, buttons, zippers, adhesives, pinch valves, or the like.

In some variations, the shape or design of the fluid passageway may be chosen to regulate the flow of fluid through the fluid passageway. For example, the fluid passageway may be configured so that a pressure drop of a fluid moving through the fluid passageway is minimized as the fluid moves through the fluid passageway. Thus, the inner diameter or the fluid passageway may be relatively constant. In some variations, the flow of fluid though the fluid passageway may be regulated to slow or speed up fluid flow over some regions of the fluid passageway.

In general, fluid moving through the fluid passageway is temperature regulated, and the fluid passageway may comprise at least a portion having a thermal conductivity to permit the exchange of thermal energy between fluid in the fluid passageway and an outer surface of the fluid passageway (and thereby a subject using the device). Thus, the walls (or a portion of the walls or sides) of the fluid passageway may be made of a material that permits the exchange of thermal energy across the walls of the fluid passageway. The size (e.g., thickness) of the walls of the fluid passageway may also be configured to permit transfer of thermal energy. The shape, size, or other dimensions of the fluid pathway may also be configured to regulate or control the thermal conductivity over all or a region of the temperature-controllable device. For example, the fluid passageway may be configured as a countercurrent exchange pathway.

The flow of fluid through the fluid passageway (or a region of the fluid passageway) may also be regulated based on the temperature of the fluid flowing within the fluid passageway. Thus, flow of fluid within the fluid passageway may be adjusted manually or by responsive (e.g., temperature-sensitive) elements within the fluid passageway. For example, temperature sensitive valves such as bi-metal, bi-metal snap disks, thermal expansion valves (e.g., wax expansion valves, plastic expansion valves, etc.), expanding coils, or any other appropriate temperature-reactive component may be used.

Changing the flow of fluid within the fluid pathway may result in regions of the fluid pathway that have different pressures relative to other regions of the fluid pathway. Changing the flow (and/or the pressure) within all, or a region, of the fluid passageway may also regulate the active size of the pad. Pressure differentials within the fluid passageway may also be used to create pulsatile flow within the entire fluid passageway, or just in a region of the fluid passageway. Thus, the fluid passageway may be configured to permit or create pulsatile flow. Pulsative flow may be desirable, for example, to drive out edema in a subject suffering therefrom. For example, a pressure-regulating valve may be placed within the fluid passageway (e.g., at the entrance or exit, or within a region of the fluid passageway) to create high-pressure and low-pressure cycles of fluid flow.

The fluid passageway may be configured to conform to a subject's anatomy. As used herein, a subject may be any appropriate or intended user of the temperature-controllable device. For example, a subject may be a patient (e.g., a patient recuperating from an injury or a surgery). In some variations, the fluid passageway may comprise an outer surface configured to contact a region of a subject's anatomy. The outer surface of the fluid passageway may be configured to directly contact a subject, or it may be configured to interact with another contact surface, or both.

The temperature-controllable device may include a fluid passageway having an outer surface that is configured to optimize contact with a subject. For example, an outer surface of the fluid passageway may be textured. The outer surface of the fluid passageway may be any appropriate texture to enhance contact with the subject. Examples of textures include, but are not limited to: smooth, dimpled, creased, ridged, corrugated, crimped, furrowed, knitted, puckered, wrinkled, pleated, and any combination thereof. In one variation, a surface of a fluid passageway is dimpled, which may enhance contact between the outer surface of the fluid passageway and a subject's skin surface. The shape of the outer surface of the fluid passageway may be regular or irregular, and there may be a variety of different shapes (e.g., "dimples" or projections) of different sizes. The dimples may be collapsible. In another variation, the surface area of an outer surface of a fluid passageway may be flat, to maximize the amount of contact with a subject's skin.

In some variations, the outer surface of the fluid passageway is textured to enhance contact with a subject-contacting surface. For example, the outer surface may include interlocking projections or regions that interlock with a contact surface to permit attachment of the additional surface such as a subject-contacting surface (for example, a pad). Any appropriate method may be used to shape or texture the outer surface of a fluid passageway. For example, the outer surface may be textured by vacuum forming techniques, and the like.

The fluid passageway of the temperature-controllable device may have an overall shape that enhances contact with a subject's anatomy, or that enhances comfort when used or worn by a subject. For example, the fluid passageway may have a non-uniform thickness that is configured to conform to a region of a subject's anatomy. In some variations, regions of the fluid passageway may be more or less pliable, permitting the temperature-controllable device (or at least the fluid passageway portion) to adapt to fit a subject, or a range of subjects.

B. Fluid Supply Unit

Any appropriate fluid supply unit may be used to supply fluid to the fluid passageway for regulating the temperature of the device. Thus, the fluid passageway may be connected to a temperature-regulated fluid supply unit that is configured to heat or cool the fluid and controllably pump the fluid within the fluid passageway. The fluid supply unit may comprise a single device that both regulates the temperature of the fluid and pumps the fluid, or the fluid supply unit may comprise separate devices to regulate the temperature and pump the fluid. Examples of commercially available temperature-regulated fluid supply units may include the Seabrook SMS-5000, the Gaymar TP-500, etc. In some variations, the temperature of the fluid may be actively regulated (e.g., cooled or heated), and may be controlled so that the temperature is held at a set level. In some variations, the temperature of the fluid may be passively regulated or may be unregulated (e.g., using an ice bath). The fluid supply may controllably pump fluid within the fluid pathway. For example, the pump may allow control of the rate of fluid flow, or the kind of fluid flow (e.g., the steady-state, pulsatile, etc.).

Similarly, any appropriate fluid may be used within the fluid passageway. For example, water may be used, including water containing additional compounds when desirable (e.g., salts, active agents, etc.). The fluid may be a liquid, a gel, a suspension, a heterogeneous mixture of compounds and/or fluids, or the like. The fluid may also include an antifreeze. More than one type of fluid may be used. For example, a fluid having a high viscosity and a high thermal conductivity may be used with a fluid having a low viscosity. The fluid may have beneficial thermal properties for transferring heat to and from a subject through the fluid passageway. For example, the fluid may have a high thermal conductivity.

C. Splint

The temperature-controllable device may include a splint region. A splint may support the fluid passageway, a portion of the subject's anatomy, or both. Furthermore, the splint may be re-formable, so that it is moldable to at least a portion of a subject's anatomy, and then may later be moldable to a different portion of a subject's anatomy or conformation. In some variations, the splint is settable, so that it may be molded into a first shape (e.g., conforming to a subjects anatomy) and "set" into this shape. Later the splint may once again be molded and set into a desired position. In one variation, the splint material or structure may be activated to allow molding and setting, and once set, the splint may be re-activated so that it can again be molded and set into another desired position. For example, the splint may comprise a material that is heat activated, which allows the splint to be molded into a desired shape when the splint is within an activation temperature range (usually a range that is outside of the normal usage range for the splint). When the temperature is below the activated temperature range, the splint may substantially maintain its "set" shape. This splint may be re-formed by changing once again holding the splint at a temperature within the activated temperature range. Even when the splint is set, in some variations it may remain somewhat flexible (or even elastic).

In some variations, the splint may be molded to a subject's anatomy using mechanical connections that may be locked into place ("set"). For example, the splint may comprise a jointed framework. The joints may move to shape or position the splint against a subject, and these joints may then be locked into place.

A splint may provide structure for the fluid passageway. For example, the splint may be attached to the fluid passageway region, or to a portion of the fluid passageway region. In some variations, the splint bends or shapes the pliable fluid passageway region so that the fluid passageway region may be secured against a portion of a subject's anatomy. The fluid passageway region and the splint may be attached in any appropriate manner. Thus, a splint may be directly or indirectly secured to a fluid passageway region. In some variations, the splint region is attached directly to an outside surface of the fluid passageway (e.g., by an adhesive, a holdfast or any other appropriate attachment, as described herein). In some variations, the splint region is held by an attachment guide (e.g., a pocket, or frame) that is also attached to the fluid passageway.

The splint may also be releasably secured to the fluid passageway, and any appropriate fastener may be used. For example, the splint may be held adjacent to a portion of the fluid passageway region by an adhesive (e.g., a temporary adhesive or a releasable adhesive), a tie, a button, a hook and latch attachment (e.g., VELCRO™), a snap, a belt, a rivet, zipper, a magnet, a friction-fit, etc. The splint may also be permanently secured to the fluid passageway.

The splint and the fluid passageway region may also be arranged in any appropriate manner. In some variations, the fluid passageway is configured to be closer to (or even touching) a portion of a subject's anatomy than the splint, when the subject is wearing the temperature-controllable device. In some regions, the splint may be closer to (or even touching) a portion of a subject's anatomy than the fluid passageway region, when the subject is wearing the device. In some variations, the splint may be held within the fluid passageway. Thus, the splint may also have thermal properties appropriate for transferring heat between the fluid passageway region and a subject's anatomy. For example, in an embodiment of the splint in which the splint contacts a portion of the subject's anatomy as well as the fluid pathway region, the splint may comprise a thermally conductive material. In some variations of the temperature-controllable device, a splint may comprise an insulating material. Splints comprising insulating materials may be useful when the splint is attached to an outer surface of the fluid passageway region that does not contact a subject's anatomy.

The splint may also be configured to apply or modify the pressure within the fluid passageway, or the pressure against the subject. For example, the splint may compress the fluid passageway region, including compressing the fluid passageway region against a subject. In some variations, the splint restricts expansion or movement of the fluid passageway region. The splint may also compress or support a portion of the subject's anatomy, without compressing the fluid passageway region.

The splint may be made of any appropriate material (or combination of materials). For example, the splint may be made of a metal, a ceramic, a polymeric material, or any combination thereof. In some variations, the splint comprises a thermoplastic material (e.g., acetal, acrylic, cellulose acetate, nylon, polyethylene, polystyrene, vinyl, nylon, polypropylene, etc.) that may be re-formed. In some variations, the splint may comprise a metal (e.g., aluminum, stainless steel, tin, alloys, etc.) Additionally, some (or all) of the splint may be made of a pliable material (e.g., a wax, rubber or other elastic material). In some variations, the splint comprises a thermoset plastic or an injection molded plastic. The splint may be a composite of materials and may be solid, hollow, porous, or contain cavities or passages therethrough. For example, the splint may comprise a matrix, e.g., a honeycomb geometry. Passages (or holes) through the splint may decrease the weight, and may provide attachment sites (e.g., for securing the splint or for securing other components to the splint) or other functional sites. The splint may also be perforated. Perforations may allow deformation of the splint.

A splint molding tray ("tray") may be used to help mold or form a splint region of a device to conform to a subject's anatomy. For example, when the device comprises a splint made of a thermoplastic material, a molding tray may be set to a temperature above the activation temperature of the thermoplastic material, so that the thermoplastic material becomes pliable and may be molded (e.g., formed or re-formed) to conform to a portion of a subject's (e.g., face). Some variations of the molding tray comprise a fluid bath region for holding a fluid (e.g., water) that may be at a temperature above the activation temperature of the thermoplastic material from which a splint is made. The molding tray may include a holder for holding the device (or the splint portion of the device) submerged beneath a fluid in the tray. For example, a holder may include a clip, a strap, a grasper, a cage, etc. In some variations, the tray may also include an indicator, indicating the temperature of the device. In some variations, the tray may include a fill line, indicating the level to which the fluid should be filled. The tray may also include a heater, for regulating the temperature of fluid in the molding tray. Thus, the molding tray may be used to raise the temperature of a splint (in variations of the device comprising, e.g., thermoplastic splints) above an activation temperature for a splint, permitting the splint to be formed or re-formed. A person using the tray can then remove the device, and mold the device containing the splint (or simply the splint region) to a portion of a subject's anatomy on which the device will be applied. The tray is not limited to molding thermoplastic splint materials. Any appropriate splint may be used with a molding tray (e.g., wax, etc.).

The splint may also comprise one or more textures or textured surfaces. The splint may comprise a surface that is smooth, dimpled, creased, ridged, corrugated, crimped, crinkled, furrowed, knitted, puckered, wrinkled, and combinations thereof. A texture may enhance the ability of the splint to conform to a surface (e.g., a subject's anatomy, or the fluid passageway), or to transfer heat, or to connect to another surface.

In some variations, the splint comprises a pressure-adjustable splint. For example, an inflatable splint (or splints) may be used. Thus, the splint may comprise an inner region that may be inflated with either a gas (e.g., air), a liquid (e.g., water, including pressurized water), gels, etc., or the like. A valve may be used to regulate the amount of pressure in the splint (and therefore the "stiffness" of the splint). A splint may comprise multiple pieces, or be made of multiple splints, which may be composed of different materials and may be of different geometries.

D. Layers

In some variations, the temperature-controllable device may comprise three or more layers. The layers may be attached to each other to form two or more pockets or "bladder" regions between the layers. A bladder region may be substantially sealed (e.g., with one or more inlet and outlet) and configured as the fluid passageway region. An additional pocket region may be configured to hold a splint.

For example, a temperature-controllable device may comprise three layers. The first two layers may be fluid-resistant (e.g., "waterproof") layers that are made from sheets of a pliable film. The edges of the pliable film may be bonded together in the shape of the fluid passageway region, to form a water-tight bladder. The third layer may be (at least partly) bonded to the first and second layers to form another bladder or pocket. The third layer may be made from the same material as the first two layers, or it may be made from a different material. The layers may be bonded together by any appropriate technique, and the choice of bonding technique may depend, at least in part, on the material selection of the layers. Exemplary bonding techniques include (but not limited to) rf-welding, heating, using an adhesive, snap-fitting, zipper-fitting, combinations of the foregoing, and the like. The second pocket, formed by the third layer and the first (or second) layers, may be used to hold a splint, or it may form a splint (e.g., a pressure-adjustable or inflatable splint). The second pocket may be sealed (e.g., once the splint is inside) or it may be left open, so that a splint (or other structure) may be removable from the pocket. The layers may be of different sizes and be made of different materials.

Thus, the first pocket, formed by the first and the second layers, may be configured as a fluid passageway region. The second pocket (formed by the third layer and the second layer) may be configured as an insulator. For example, in some variations, the second pocket is inflated to provide an insulating layer of air. The second pocket may also hold an additional material, such as an insulating material. The second pocket may also include a fastener (e.g., an adhesive, strap, etc.) to secure material (including the splint) within the second pocket.

In general, the temperature-controllable devices described herein may include any of the features (e.g., the splint, pocket, attachment sites, pads, etc.) described herein in any appropriate arrangement, including layers. FIGS. 1A to 1E show cross-sections of possible configurations that may be appropriate for temperature-controllable devices. These illustrations depict just an illustrative sample of the many possible relationships that the fluid passageway region, the splint (or a portion of the splint), and any other portions may have relative to each other. While these figures depict co-extensive regions, the regions need not be co-extensive relative to one another. Indeed, in certain circumstances it may be desirable to have areas of the fluid passageway region that are not co-extensive with the splint, and that are not co-extensive with any other regions (e.g., pads, adhesives, contact surfaces, etc).

As noted above, the fluid passageway region is configured to allow fluid to flow therethrough. Any appropriate fluid may be selected for use with the devices described herein (e.g., water). The fluid passageway region and the splint may have any number of configurations relative to one another. Making reference now to FIG. 1A, there is shown a temperature-controllable device (100) comprising a splint (102), a fluid passageway portion (106) and an additional portion (108). In this variation, splint (102) is positioned adjacent to the fluid passageway region (106). The fluid passageway region may be attached or adhered to splint (102), but need not be. Attachment of the fluid passageway region to the splint may be accomplished using any number of appropriate methods. For example splint (102) may be adhered to fluid passageway region (106) via crimping, heat molding, friction fits, zipper fits, or surgical adhesives, glues, or the like. In this variation, the fluid passageway region is configured to contact at least a portion of a subject's anatomy (e.g., face, nose, etc.), and is also configured to be moldable thereto. Similarly, splint (102), which in this variation is not in direct contact with the subject, is configured to be moldable to at least a portion of the subject's anatomy in order to provide the proper stabilization and to provide adequate pressure thereto.

Additional portion (108) may serve any number of functions. For example, additional portion (108) can comprise an adhesive, where the adhesive is configured to contact at least a portion of the subject's skin and temporarily adhere the device to the subject. An adhesive may be used instead of, or in addition to, other mechanisms of securing the device to a subject's anatomy (e.g., headbands, flexible members, Velcro™ straps, and the like). Similarly, the additional portion (108) may comprise a sterile portion, where the sterile portion is configured to contact at least a portion of the subject's skin. In this way, the subject is contacted by a sterile portion, which may help to reduce the risk of infection and protect against the application of bacteria and other debris to an injured area. The sterile portion may be made from any number of appropriate materials. For example, the sterile portion may be made, at least in part, from a sterile material selected from the group consisting of gauze, cotton, paper, plastic, polyurethane, silicone, polypropylene, and mixtures thereof. Of course, the additional portion (108) may also be both sterile and adhesive.

Figure 1B:
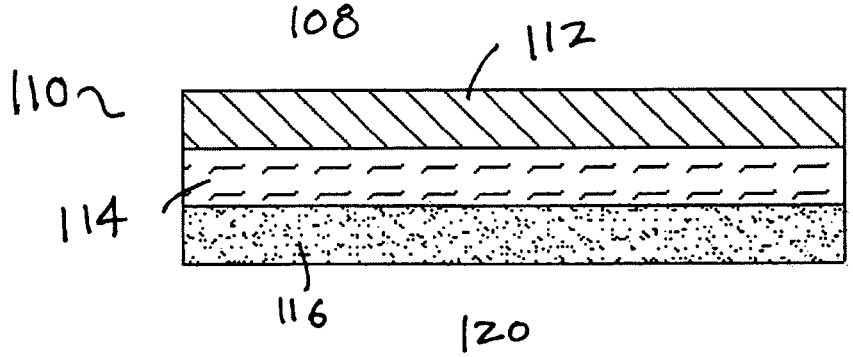

FIG. 1B depicts another variation of the device in which a viscous liquid portion (e.g., a gel, wax, etc.) is used. As shown there, device (110) comprises a splint (112), a fluid passageway region (114) and a viscous liquid portion (116). As with the device (100) described above, the splint (112) of this device (110) is not immediately adjacent to the subject's anatomy. In this variation, viscous liquid portion (116) may be useful in providing the subject with a better fit of the device, and may provide for better heat transfer. For example, the viscous liquid portion may be a gel, wax, or other viscous material that allows for expansion in order to conform to the nose as the nose expands from additional post-surgery swelling. The viscous liquid portion may be covered by, or enveloped within a sterile portion.

Figure 1C:
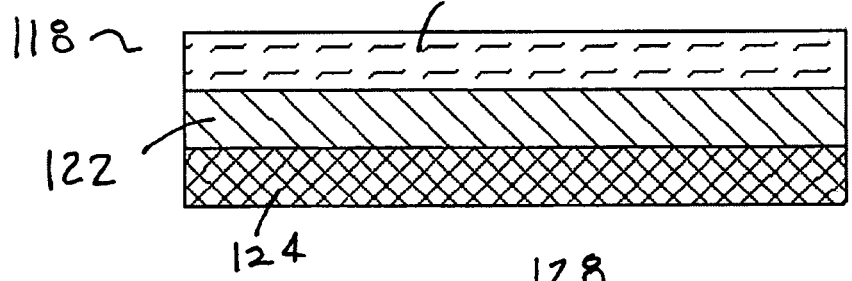

Another variation is shown in FIG. 1C where temperature-controllable device (118) comprises a fluid passageway region (120), splint (122), and additional portion (124). In this variation, the fluid passageway region is adjacent to splint (122), but is not adjacent or in contact with the subject. In this variation, as is described above, the additional portion may comprise an adhesive portion, a sterile, portion, a viscous liquid portion, or any combination thereof.

Figure 1D:
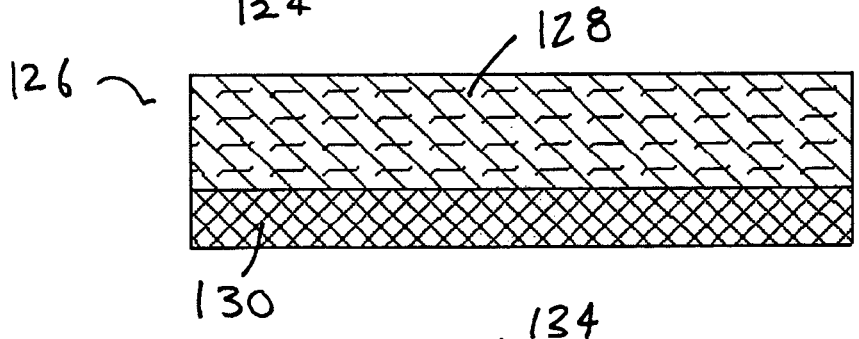

Shown in FIG. 1D is another variation in which device (126) comprises a fluid passageway region, which is at least in part, integral to the splint (depicted as combined 128). In this variation, the splint may be selected of a hollowed-out material that allows fluid to flow therethrough. Appropriate materials for the splint were described above. In this variation, the fluid flows, at least in part, through the splint itself, and provides an integrated cold (or heat) therapy splint device. An additional portion (130) is also shown, which as described above may comprise an adhesive portion, a sterile, portion, a viscous liquid portion, or any combination thereof.

Figure 1E:
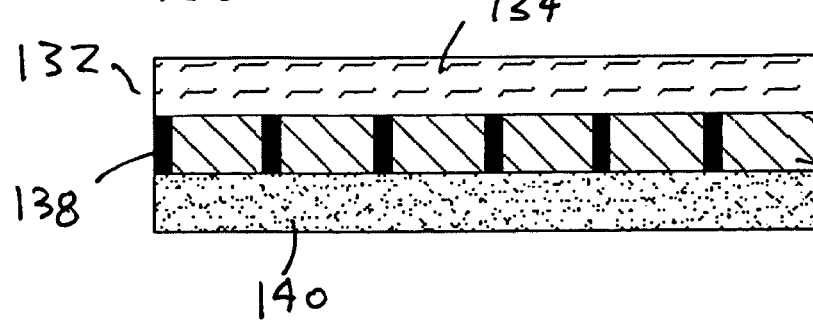

Shown in FIG. 1E is a cross-section of a device wherein the splint has perforations therein (138). As depicted there, device (132) comprises a fluid passageway region (134) a perforated splint (136) and an additional viscous liquid portion (140). As described briefly above, the perforations may provide any number of advantages. For example, the perforations (138) may reduce the overall weight of the device, or increase the thermal conductivity of the splint (136) and hence increase the heat transfer therethrough. In addition, viscous liquid portion (140) may be a viscous liquid (e.g., a gel, wax, etc.) that has the capacity to expand into perforations (138). While the viscous liquid portion need not undergo such expansion, expansion may be desirable in certain circumstances.

For example, as noted above, it is foreseeable that a portion of the subject's anatomy in contact with the temperature-controllable device may swell to some extent after surgery and after the device has been placed on the subject. Providing a viscous liquid portion that can expand into the perforations can help prevent against overpressure of the device on the subject. In addition, the viscous liquid can help ensure a proper fit. In some circumstances, it may be desirable to provide a viscous liquid that has a high thermal conductivity. In some variations, the viscous liquid has at least one metallic fragment therein, in order to increase the thermal conductivity of the viscous liquid, and consequently the device.

While not shown in the variations depictions in FIGS. 1A-1E, the temperature-controllable device may also comprise an insulating outer portion. In these variations, the insulating outer portion is typically configured to provide thermal insulation between the device and the ambient environment. For example, the insulating outer portion may be adjacent to the splint, the fluid passageway region, or their combination when the portions are, at least in part, integral to each other. In this way, the non-skin side portion of the device is thermally insulated.

In some variations of the devices described herein, the fluid passageway region may also include at least one pouch therein. As previously described, the pouch may be formed between layers of a layered structure in some embodiments of the temperature-controllable device. Thus, in some variations, the third layer may not be co-extensive with the fluid passageway region formed by the first and second layers. Multiple pouches may be formed. For example, a pouch, or pouches, may be located on the inner or outer surfaces of the fluid passageway region. In this way, the pouch may be configured to receive at least one splint therein, e.g., to provide support to an injured area.

Figure 2A:
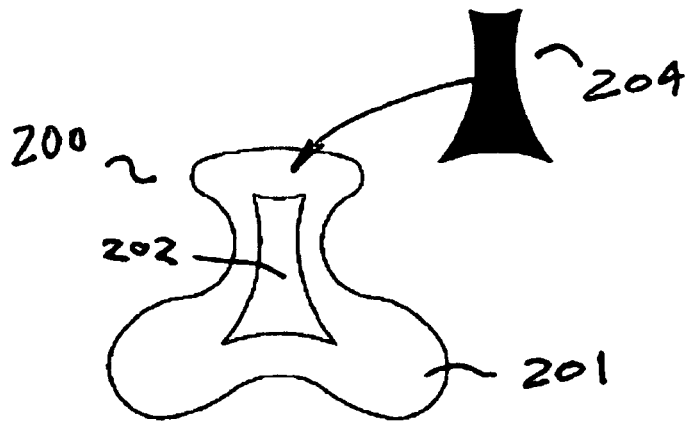
FIG. 2A illustrates a fluid passageway region having a pouch thereon, which is configured to receive a splint therein.
Figure 2B:
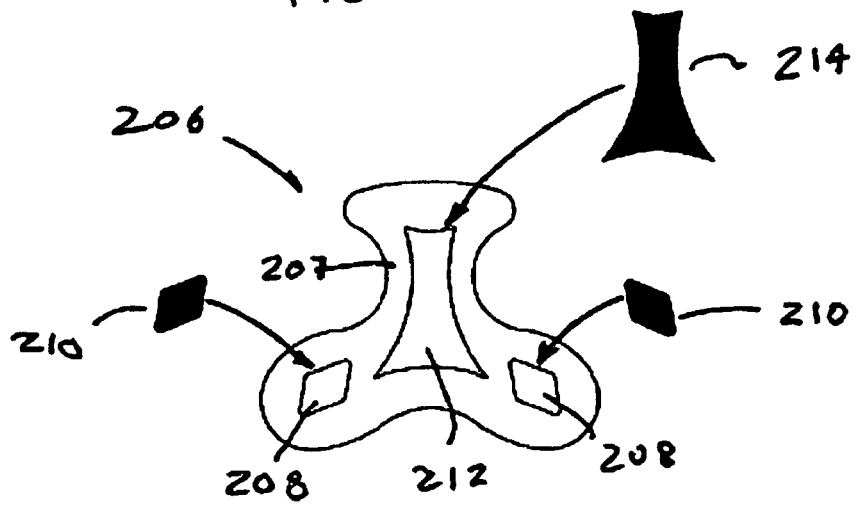
FIG. 2B shows a fluid passageway region having multiple pouches thereon, which are configured to receive splints therein.

The fluid passageway region may have any number of pouches thereon as is desirable and practical. Illustrative examples of these variations are depicted in FIGS. 2A and 2B. Shown in FIG. 2A, for example, is device (200) comprising fluid passageway region (201) having pouch (202) thereon. As shown there, the pouch (202) is configured to receive splint (204). It should be understood that the fluid passageway region of these variations may have any number configurations. While the fluid passageway regions shown in FIGS. 2A and 2B have an "inverted Y" type of configuration, they need not. That is, the fluid passageway region may have any desirable configuration. Shown in FIG. 2B is device (206) comprising fluid passageway region (207). In this variation, fluid passageway region (207) has more than one pouch thereon. For example pouches (208) are shown as configured to receive splints (210) therein, and pouch (212) is shown as configured to receive splint (214) therein.

Figure 2C:
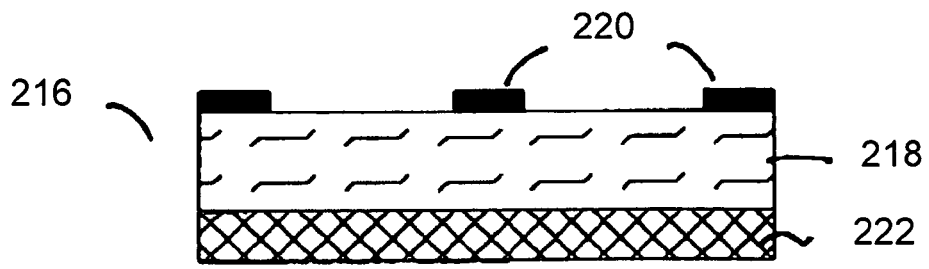
FIG. 2C is a cross-sectional view of a device comprising a fluid passageway region having multiple pouches thereon, which have splints therein.

While trapezoidal-like configurations are depicted in FIGS. 2A and 2B for the pouches and splints, it should be understood that pouches and splints may have any appropriate or desirable shape or size. In addition, the splints may be configured to contact any portion of a subject's anatomy (e.g., the nose, the ears, the chin, the cheeks, the area immediately above the upper lip, the area above the eyebrow, the area immediately under the eyes, the forehead, the entire face, breast, torso, buttocks, groin, etc.). FIG. 2C shows a cross-sectional view of device (216) that comprises a fluid passageway region (218) having pouches with splints (220) thereon.

Also shown is additional portion (222), which may comprise an adhesive portion, a sterile, portion, a viscous liquid portion, or any combination thereof.

While fluid passageway regions have been depicted herein, it is also the case that other temperature-controllable portions may be used in conjunction with a splint to accomplish the benefits herein described. It should be understood that these other temperature-controllable portions are within the scope of this invention. For example, thermoelectric modules may be embedded in the splint, or an additional portion that may be integral or adjacent to the splint, in order to provide an overall temperature-controllable device. Other types of temperature-controllable portions, which are known to skilled artisans, are also appropriate for the devices and methods described herein.

The temperature-controllable device may also comprise a contact surface for contacting a subject (e.g., contacting a subject's skin). Generally, the contacting surface may be in thermal communication with a portion of the fluid passageway region, to permit heat to be exchanged between a subject using the device and the fluid passageway region of the device (e.g., for heating or cooling). In some variations, this contact surface is sterile or sterilizable. For example, the contact surface may be made of gauze, cotton, paper, plastic, polyurethane, silicone, polypropylene, and mixtures thereof. The contacting surface may be an outer surface of the fluid passageway region, and in some variations, the contact surface may include a pad.

E. Pads

As noted briefly above, the temperature-controllable device may also include one or more pads. Thus, the device may comprise an additional region configured as a pad. In some variations, the pad (e.g., an absorbent pad) allows heat exchange between the subject and the fluid passageway region of the device. For example, in one variation, the pad is attached to a portion of the device (e.g., an outer surface of the fluid passageway) by an adhesive or other appropriate attachment mechanism or holdfast. Typically, the pad contacts the subject, and thus may help exchange heat between the subject and the fluid passageway. In some variations, a contact surface (e.g., on the outer surface of the fluid passageway) of the device is intercalated with a pad, so that the pad and a portion of the fluid passageway both contact the subject.

In some variations, the pad is an absorbent pad. Absorbent pads may be used to absorb any fluid from the subject (e.g., blood, sweat, mucus, menses, urine, etc.). For example, wound sites that may benefit from the use of the temperature-controllable device often release fluid that may need to be absorbed. Thus, a fluid absorbent pad may be used with the device. Absorbent pads may also be used to absorb fluid that leaks from the temperature-controllable device.

Absorbent pads may be made of any appropriate material, particularly materials that allow fluids (e.g. menses, blood, urine, etc.) to pass into the absorbent pad from the body, where it may be absorbed and retained by the pad. In some variations, the absorbent pad allows fluid to pass into an absorbent core of the pad, but does not allow fluid to remain on the surface of the pad, thereby keeping the pad surface (e.g., the body-contacting surface) relatively dry. Thus, a pad surface may comprise a porous surface. In one variation, the surface is a primarily a hydrophobic surface having pores which allow fluid to pass into the absorbent core.

A pad surface may comprise any appropriate material. For example, the surface may be made from woven and/or non-woven materials; polymeric materials such as apertured formed thermoplastic films, apertured or unapertured plastic films, and hydroformed thermoplastic films; porous foams, reticulated foams, reticulated thermoplastic films, and thermoplastic scrims. Appropriate woven and non-woven materials can comprise natural fibers (e.g. wood or cotton fibers), synthetic fibers (e.g. polymeric fibers such as polyester, polypropylene or polyethylene fibers); bicomponent fibers (i.e., fibers having a core of one material, which is enclosed in a sheath made of another material), or from a combination of natural and synthetic fibers. In one variation, the pad surface is a coating (e.g. a coating directly on an absorbent core), and in other variations, the pad surface comprises a flexible surface such as a thin film of aperatured material. In one variation, the pad surface is relatively soft. In one variation, the pad surface comprises a textured pattern. In one variation, the surface is comprised of a material further sufficient to contain an absorbent core material within the pad.

The pad may comprise an absorbent core comprising any appropriate absorbent material. For example, the absorbent core may comprise any of the liquid-absorbent materials commonly used in sanitary napkins and other absorbent articles, such as comminuted wood pulp (airfelt), creped cellulose wadding; meltblown polymers (e.g. coform); chemically modified cellulose fibers (e.g. crosslinked, stiffened, etc.); synthetic fibers (e.g. crimped polyester fibers); peat moss; tissue (e.g. tissue laminates); absorbent foams; sponge material (natural and artificial); polymeric materials (e.g. supersoft polymers); natural or synthetic fibers (e.g. cotton); woven and non-woven materials; absorbent gelling materials; or any combination or mixture of these. The absorbent material may also comprise (or partly comprise) less absorbent, or non-absorbent, materials such as polyurethane foam, which can be formed into absorbent structures when combined with absorbent material.

The absorbent material may be formed into a structure or structures. For example, the absorbent material of the pad may be shaped to have regions of different thickness, or to conform to a subject's anatomy, or to support a subject's anatomy. In one variation, the absorbent material is a foam (e.g. High internal phase emulsion or HIPE foam). In one variation, the absorbent material comprises pellets. Pellets of absorbent material may be connected (e.g. as in a matrix or webbing), may be loose, or may be some combination thereof. Pellets of absorbent material may be of any appropriate size and/or shape, or range of sizes and/or shapes.

The temperature-controllable device may comprise a pad (including the fluid absorbent pads described above) that are configured for single use. Thus, the pads may be disposable. In some variations, the pads are configured be replaceable on a re-usable temperature-controllable device. Although the entire temperature-controllable device may also be disposable, in some variations, the temperature-controllable device may be reused a number of times, while the pads are configured for single-use. In some variations, the pads may be reusable. In some variations, the pads are washable.

The pad may be a surface-contacting pad. For example, a surface contacting pad may comprise a textured surface (e.g., smooth, dimpled, creased, ridged, corrugated, crimped, crinkled, furrowed, knitted, puckered, wrinkled, and combinations thereof). In some variations, the pad may be a sterile (or sterilizable) pad. The pad may include a sanitary barrier between a region of the pad that contacts a subject and the rest of the device. For example, an absorbent pad may be removeably (or replaceably) attached to a fluid passageway region by an adhesive on a region of the pad which is fluid-impermeable. A pad may be attached to the temperature-controllable device (e.g., to the fluid passageway region) by a holdfast. A holdfast may be any appropriate fastening means or attachment device or mechanism. For example, the holdfast may comprise a hook and latch mechanism, a snap, a button, an adhesive, a tie, a zipper, a friction fit, a clasp, etc.

Furthermore, a pad may be configured to fit a portion of a subject's anatomy. In some variations, the pads are configurable to a subject's anatomy (i.e., a pad may be moldable to fit a portion of a subject's anatomy). For example, the pad may be shaped or supported by a splint. The pad may have a variable thickness. In some variations, the pad may conform to a subject's skin to create pressure differentials against the subject's skin, or within the fluid passageway region of the device.

In some variations, the device comprises only a pad (e.g., an absorbent pad) and a fluid passageway region, without a splint region. In some variations, the temperature-controllable devices, or regions of the temperature-controllable devices (e.g., the fluid pathway region) are washable.

One variation of the temperature-controllable device comprises a thin-film tube that has a fluid absorbing material laminated to the side (or more than one side) of the tube. The thin-film tube comprises the fluid passageway region of the device, as described above. The pad (e.g., a fluid absorbing pad) comprises the strips of laminated absorbent material on the side (or sides) of the tube. The tube may then be folded or arranged so that both the fluid absorbing material and thin-film tubing may be in contact with the subject.

F. Inlet and Outlet

The temperature-controllable device may comprise an inlet and an outlet (e.g., inlet and outlet ports) for accessing the fluid passageway region to allow fluid to continuously flow therethrough. The inlet and outlet may be configured to attach to a fluid supply unit and to the fluid passageway region. In this way the temperature-controllable device may be configured to work with any number of different fluid supply units, provided these fluid supply units have appropriate attachment points for the inlet and outlet. The ease in which the temperature-controllable devices may be connected to various fluid supply units may help improve acceptance of the devices and promote use. This is especially so because fluid supply units may be easily interchangeable with the temperature-controllable devices described herein.

In some variations, the inlet an outlet may comprise a quick-connect or quick-disconnect structure. For example, a quick disconnect may quickly connect and disconnect to a fluid supply unit. In some variations, the inlet and outlet comprise ridged fittings that can secure within tubing (e.g., tubing connected to a fluid supply unit). In some variations, the inlet and outlet comprise flanged fittings that can be secured within tubing. The inlet and outlet may also comprise tubing extending the distance that the temperature-controllable device may be used from the fluid supply unit. Similarly, the inlet and outlet may also comprise a releasable seal to prevent leakage from the connections between the inlet and outlet and the fluid supply unit.

G. Active Agents

Compounds or active agents, including medicaments, may be used with the temperature-controllable device. The device may include active agents that may be delivered to a subject, or active agents that may be provided within the fluid passageway (e.g., to prevent contamination of the device). For example, a medicament may be included on a contact surface of the device for delivery to a subject. Any appropriate active agent may be used with device for delivery to the subject. For example, active agents may include: moisturizers, surfactants, disinfectants, cosmetics, perfumes, vitamins, acids, bases, pharmaceuticals, or an anesthetic. Furthermore, any appropriate formulation containing an active agent may be used. For example: creams, a petroleum-based products, alcohol-based products, or the like.

An active agent may be delivered from any portion of the device to a subject, but especially surfaces that contact a subject using the device. For example, the active agent may be applied to a pad used with the device. In one variation, the device comprises a medicated pad (e.g., a pad from which the active agent may be released) and a fluid passageway region. In some variations, the device may be particularly useful for delivery of active agents that are temperature sensitive. Thus, the fluid passageway region may be used to regulate the temperature of the pad so that the active agent is kept at or about some optimal temperature (e.g., a temperature optimal for delivery, efficacy, or stability of the active agent). For example the rate of delivery of a drug such as by transdermal delivery may be affected by temperature variations. In addition, a medicated pad may further include a protective cover preventing premature release or exposure of the active agent. The protective cover may be removed (e.g., peeled off) before using the medicated pad.

Furthermore, active agents may be provided within the device to prevent contamination of the device. For example, the inside of the fluid passageway region may include an active agent. For example, active agents such as an antibacterial, an antifungal, an antimicrobial, a perfume, a dye, a lubricant, an anti-corrosive, an antifreeze, an antimolding agent, and any mixtures thereof, may be included. Active agents may be added to the fluid in the passageway, or they may be released from the passageway itself, for circulation (e.g., continuous circulation) in the passageway. For example, active agents may be coated on the inner walls of the fluid passageway region, or merely located within the fluid passageway region. When fluid is added to the fluid passageway region (e.g., after connection to the fluid source unit), an active agent may be added to the fluid. In some variations, an active agent may be embedded or impregnated within the walls of the fluid passageway. The addition of active agents within the device may improve the performance of the device, or extend the lifetime of the device. For example, a lubricant or anti-corrosive may be included to benefit the fluid pump. Thus, in variations of the device in which the addition of fluid to the device releases a beneficial active agent, each use of the device may help prolong the lifetime and operation of the device and its corresponding fluid supply unit.

H. Attaching the Temperature-Controllable Device to a User

The temperature-controllable device may include a support structure for supporting the device when the device is worn by a subject. Thus, support structures may support the weight of the device and may help secure the device to the subject. In some variations, the support structures may be straps for supporting the weight of the device (e.g., the fluid passageway region, the inlet and outlet, and any attached fluid source supply lines). Straps may comprise elastic straps that are fastened to a portion of the device and worn by the subject. The straps may be attached to the device by any appropriate method. For example, an outer surface of the device may comprise an attachment surface for mating with an attachment site from a strap or other support structure. In some variations, the outer surface of the device comprises a flocked attachment surface (or a "loop" region) compatible with a hook region for attachment thereto.

Figure 3:
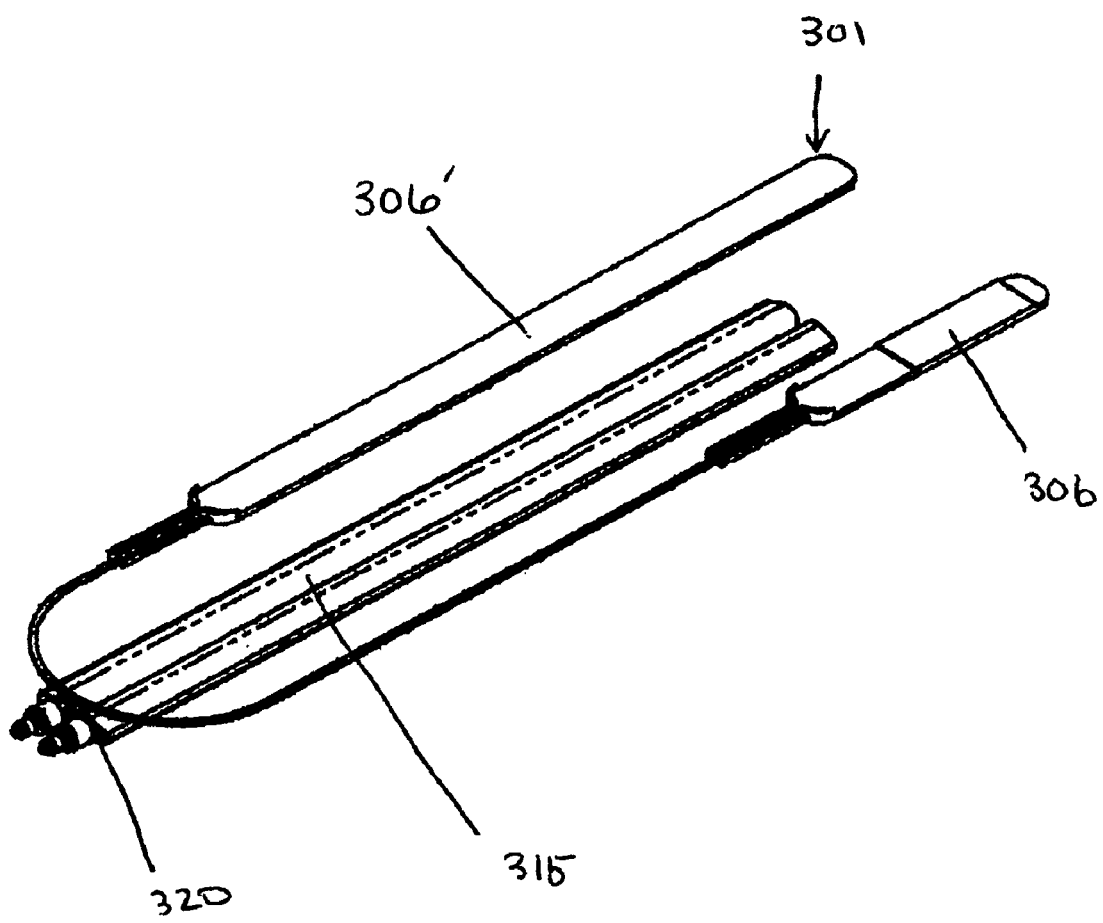
FIG. 3 is a perspective view of a neck strap and connection tubing.

Thus, a strap may be used to secure the device to the subject. Any other appropriate support structure may also be used. Support structures (such as straps and the like) may be adjustable, so that they may be used with subjects of different sizes. FIG. 3 shows an example of a strap that is configured as an adjustable neck strap (301). The neck strap may include a string region, and also an attachment region (306, 306') for securing the ends of the neck strap around the subject's neck. The string region may be connected to a portion of the device, such as the tubing connecting the device to the fluid supply unit (315). In variations of the device configure to attach to a subject's head or face, the neck strap may be connected (e.g., via the string) to a distal end of the tubing (320), therefore allowing the weight of the tubing to be borne by the neck strap rather than the portion of the device attached to the subject.

In some variations, the support structure comprises a garment that may be worn by the user. For example, the support structure may comprise a stocking, a shirt, a sleeve, shorts, pants, a girdle, or any other appropriate garment that may be worn by the user to support the temperature-controllable device. In one version, the garment comprises a cap (e.g., a stocking-type cap) that covers part of the head. The garment may comprise attachment sites, or attachments, or may be made of a material that permits easy attachment to the temperature-controllable device. For example, the garment may include an adhesive or adhesive regions. In some versions, the garment may attach to additional support structures (e.g., straps, etc.). The garment may be loose fitting or tight fitting. In some versions, the garment may provide additional support to the body region being treated, or to adjacent body regions. In some versions, the support structure (e.g., the garment) may be thermally conductive, to allow the temperature-controllable device to be placed over the support structure, so that the support structure contacts the patient, and heat is exchanged with the temperature-controllable device through the support structure. For example, the support structure may comprise a bandage or garment worn by the user that covers all or a portion of the injured region, and the temperature-controllable device may be attached to the support structure to provide a therapeutic effect therethrough.

In some variations, the support structure comprises a frame. For example, temperature-controllable devices configured for use on a subject's face may be attached to an eyeglass-like frame configured to be worn over a subject's ears to help support the weight of the device. The frame may be made from any appropriate (e.g., lightweight, strong and durable) material, such as a metal (e.g., aluminum). A support structure may also comprise a headband. In some variations, the headband and the frame may comprise a material which is bendable (e.g., a metal, such aluminum) and thus may be adjusted to better fit a subject.

In some variations, the support structure does not directly attach to the device to the subject, but instead helps support the weight of the device, which may make the device easier for a subject to use. For example, the temperature-controllable device may include a fastener (e.g., an adhesive, clip, etc.) for attaching the device to a garment to be worn by the subject. Thus, a support structure may be used to secure the device in areas that may be otherwise difficult to secure devices (e.g., the shoulders, breasts, etc.). In some variations, the support structure may support the device without directly connecting to the subject or to portions or the device that are connected to the subject. For example, a support structure may attach the device to a pillow or article of bedding near the subject. In these variations, the subject does not need to bear the majority of the devices weight.

I. Insulators

The entire temperature-controllable device (or any portion thereof) may be insulated to prevent the exchange of heat with the device, particularly with the fluid passageway region. Any appropriate method of insulting the device may be used, including the addition of an insulation layer around a portion of the device.

In some variations, the contact surface of the device is selectively insulated to control contact with the subject. Thus, an insulating mask region may be used to select the shape or size of the contact portion of the device contacting a subject's anatomy. For example, an insulating mask may be positioned adjacent to the fluid passageway region for selectively exposing a portion of the fluid passageway region to a subject (e.g., a subject's skin).

J. Use of the Device

In operation, the temperature-controllable devices described herein may be used to treat a portion of a subject's anatomy. Generally, the devices may be use by applying a temperature-controllable device to a portion of a subject's anatomy in need of treatment, and controlling the temperature of the device so as to provide therapeutic benefit. Thus, treatment may include heat therapy, cold therapy, or some combination thereof. In addition to the temperature, the fluid flow through the device may also be controlled. For example, a subject may benefit from the use of increased or pulsatile pressure through the device, once it has been applied. Thus, treatment may also include pressure (or massage) type therapies. In some variations, the device may be used for continuous treatment (e.g., over an extended period of time). In some variations, the device may be used for acute treatment.

The device may also be used to apply an active ingredient, such as a medicament, by applying the device comprising an active ingredient and a fluid passageway region to a subject in need of the active ingredient, and controlling the temperature of the device.

In particular, the device may be used to treat external portions of a subject's anatomy, including (but not limited to) the face, head, neck, torso, breasts, buttocks, groin, lets, hands and feet. The device may also be used to treat any condition that may benefit from such temperature therapy as may be applied by the device (e.g., cold- or hot- therapy). For example, the devices described herein may be useful postoperatively. In some variations, the devices may be used following cosmetic surgeries, such as rhinoplasty, liposuction, face lifts, breast augmentation, blepharoplasty, etc.

In some variations, the splint may be formed (or re-formed) to fit a portion of a subject's anatomy, or to fit a temperature-controllable device (comprising the splint) to a portion of a subject's anatomy. A method of molding the splint may include placing the splint or a device having a splint into a container holding a fluid (e.g., water) heated to a temperature above the activation temperature of the splint. For example, the previously-described molding tray may be used. The activation temperature may be a temperature above which the splint (or a portion of the splint) becomes moldable. For example, if the splint is made using a plastic such as Aqueplast, or Klarity®, the activation temperature may be between about 150-160° C. (65-70° C.). The device (or the splint portion of the device) may thus be immersed into water heated to this temperature range for about 1-2 minutes until the splint material becomes soft and relatively pliable. The device may them be removed from the water and dried. The device may then be slightly cooled (e.g., for 10-15 sec) and placed onto a subjects anatomy or otherwise molded into the desired shape. Light pressure may be applied while the thermoplastic material is setting. The splint region may then cool until the temperature falls below the activation temperature, and the material has set.

K. Kits

The temperature-controllable devices and fluid supply units described herein may be included as part of a kit. For example, a kit may include a temperature-controllable device as well as instructions for using the temperature-controllable device. Similarly, a kit may include a fluid supply unit for supplying fluid at a regulated temperature and flow rate along with the temperature-controllable device with or without instructions. In some variations, the kit may also include a splint molding tray for molding (or re-forming) the splint.

L. Illustrative Temperature-Controllable Devices

The temperature-controllable devices described herein may be used in a variety of applications, and may be used to treat a variety of conditions, including postoperative recuperation, sports therapy, drug delivery, and any other condition which may benefit from temperature therapy (e.g., cold or heat therapy). Descriptions of appropriate temperature-controllable devices and methods of using temperature-controllable devices are provided throughout this application. The description of the following temperature-controllable devices is intended only to illustrate, and is not intended to be limiting.

Nasal Temperature-Controllable Devices

The devices and methods described herein may prove especially useful in treating an injured nose, for example, one that has been injured by rhinoplasty. During a typical rhinoplasty procedure, the nose is reshaped via a process that typically involves making surgical incisions, removing cartilaginous humps, narrowing the nasal bones, and reshaping of the nose form. After this procedure has been performed, a splint is applied to the newly shaped nose in order to hold the nasal bones in their final position as they heal. The splint serves the purpose of providing stability to the nose, and the bones therein, by insuring adequate pressure is applied thereto. In addition, the splint provides somewhat of a protection mechanism against contact. In simple terms the splint is much like a cast that is applied to a broken bone. That is, the splint, like a cast, should be designed to insure accurate bone positioning and stabilization of the injured area. We note at the outset that rhinoplasty procedures typically also involve soft plastic "splints" or gauze-like materials, which are placed up the nostrils of a subject after surgery in order to help control bleeding and provide additional support to the injured area. As described in more detail below, both types of splint-type structures may find application in combination with the methods and devices described herein.

As noted above, the devices of the present invention may have particular use in post-operative rhinoplasty recovery. In a broad sense, these devices provide the dual function of splinting the nose, while allowing direct cooling to be applied thereto. As will be described in more detail below, the devices can have any number of configurations, and accordingly, these devices can be adapted specifically to the type of procedure, or procedures being performed.

Figure 4:
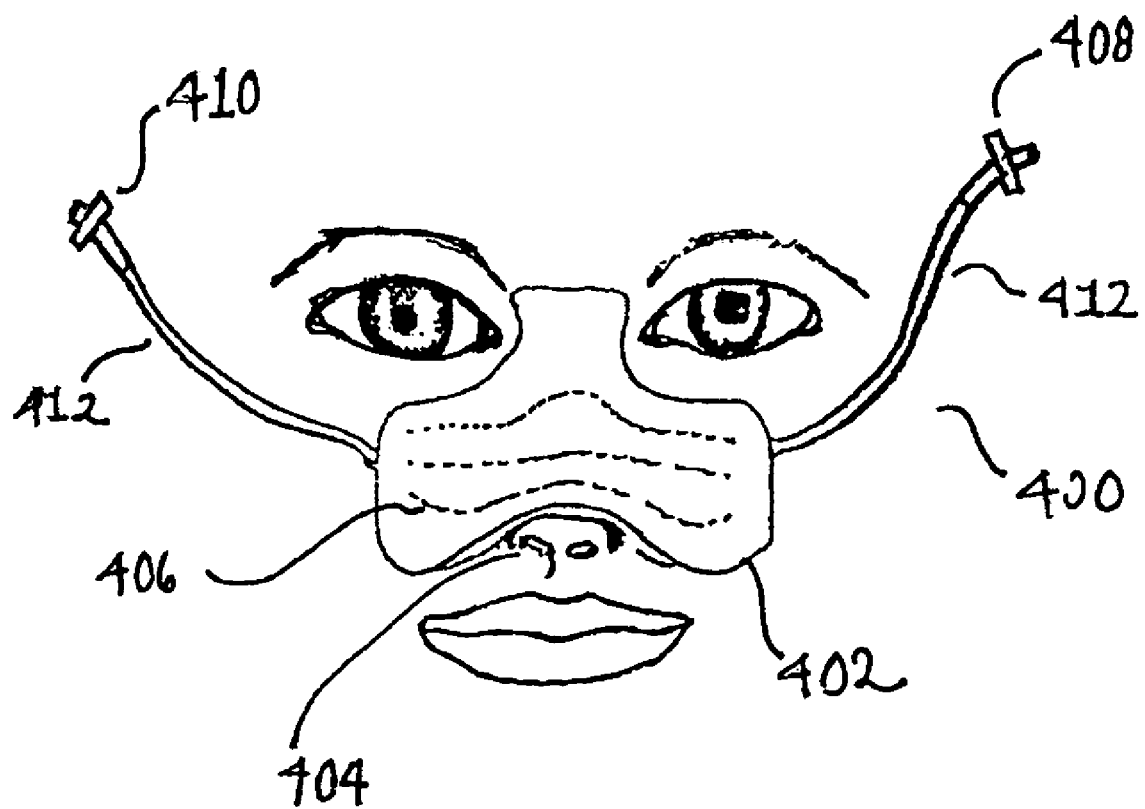
FIG. 4 depicts one example of a temperature-controllable device as described herein.

FIG. 4 shows an illustration of a device (400) appropriate for use as described herein. As shown in FIG. 4, device (400) comprises a splint (402) and a fluid passageway region (406). Also shown in FIG. 4 are inlet and outlet ports (410) and (408) respectively. These inlet an outlet ports provide for the inlet and outlet of fluid to the fluid passageway region (406). Typically, these inlet and outlet ports are configured as quick disconnects, which as the name implies, can quickly connect and disconnect to a fluid supply unit. While the inlet and outlet ports are illustratively depicted at the ends of a flexible element (412), they need not be. Indeed, these ports (410, 408) may be located at any convenient place along the device, and their location is merely a matter of design preference.

As shown in FIG. 4, the splint (402) is moldable to at least a portion of the subject's nose (404) and thereby helps stabilize and provide adequate pressure to the nasal bones after operation. The fluid passageway region (406), here depicted by dashed lines, is configured to allow a fluid to flow therethrough. In this way the temperature of the fluid may be controlled, and direct application of cold therapy to the injured area can be accomplished. It should be noted that while a direct type of path has been depicted for fluid flow through fluid passageway region (406), this is merely illustrative in nature. Indeed, the flow path may take a variety of different forms. For example, the flow path may include eddy currents, or may be of a general serpentine nature, or the like.

While the splint (402) of FIG. 4 has an "inverted Y" type of configuration, it need not be configured as such. Indeed, the splint may have any number of configurations, and have any number of different shapes and sizes. The shape and size of the splint, for example, may be determined in part by the shape and size of the subject's nose, and by the type of surgery performed. Additional illustrative splints are depicted in FIGS. 5A-5I.

Figure 5A:
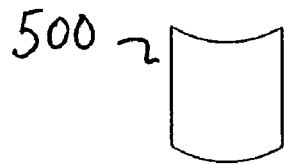
FIGS. 5A-5I depict various splint configurations appropriate for use with the devices described herein.
Figure 5B:
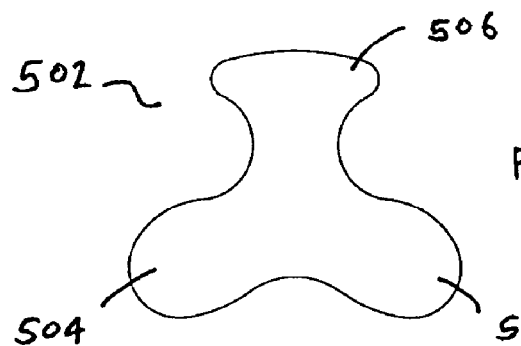

As shown in FIG. 5A, the splint (500) may have a simple semi-cylindrical type of configuration, designed to fit over the nose. The splint (500) may have any length or width as desirable for proper stabilization and pressure application. For example, the splint (500) may cover the bridge of the nose alone, may extend down to the nostrils, or the like. The "inverted Y" type of configuration is again depicted in FIG. 5B. Shown in FIG. 5B is a splint (502) having base portions (504) and bridge portion (516). The base portions (504) may extend downward and outward to cover and stabilize the soft cartilaginous areas of the nose, and bridge portion (506) may extend upward to cover and stabilize the nose bridge. As with splint (500) described above, splint (502) may be of any appropriate size, and portions (504) and (506) may extend for any desirable length.

Figure 5C:
Figure 5D:
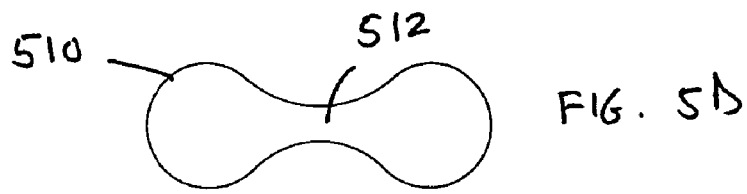
Figure 5E:
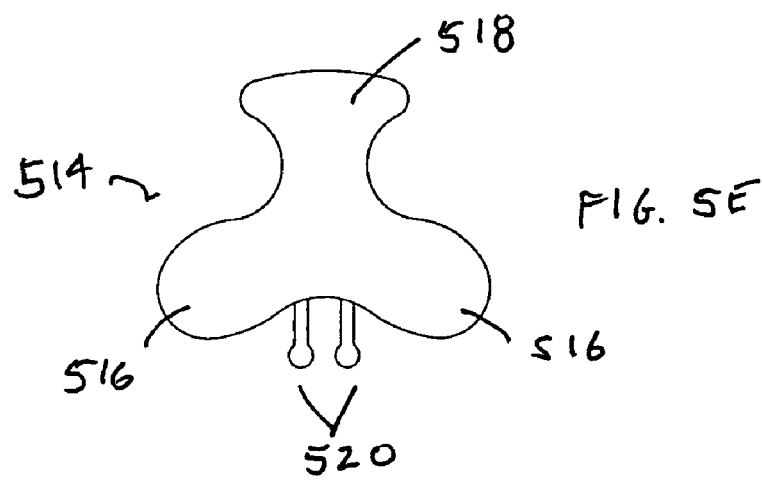

Shown in FIG. 5C is another variation of the splint where the splint (508) has a trapezoidal type of shape. FIG. 5D depicts a variation of the splint where the splint (510) has a narrowed bridge portion (512). As noted briefly above, soft nasal splints are often placed up the nostrils after rhinoplasty to control the bleeding and to further stabilize the injured area. FIG. 5E depicts a variation where soft nasal splints (520) can be attached to the splint (514). In this way, and as will be described in more detail below, the temperature of nasal splints (520) may be controlled using the fluid passageway region to help reduce the internal swelling and bruising caused by the procedure. Also shown in FIG. 5E are base portions (516) and bridge portion (518), similar to those portions described above when reference was made to FIG. 5B.

Figure 5F:
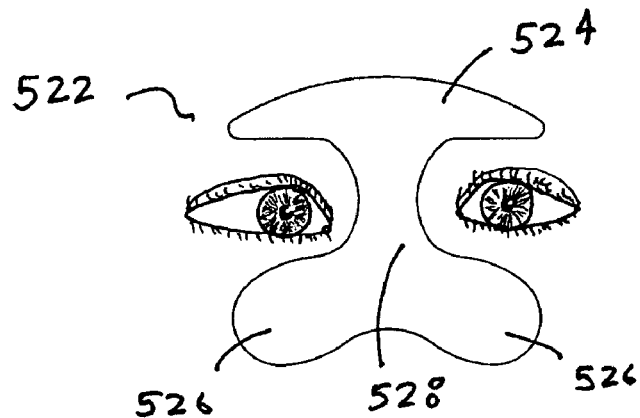

FIG. 5F depicts a splint (522) that has been configured to cover and stabilize more than one area of the anatomy. Here, splint (522) comprises eye portion (524) that is configured to mold or conform to the area immediately above the eyes. Of course, it should be noted that eye portion (524) may be extended upwardly to cover additional portions of the upper face, and indeed, the entire forehead, if desirable. Splint (522) also comprises base portions (526) and bridge portion (528), which as described above, may be extended as desirable. In addition, while splint (522) is depicted with eye portion (524) connected to base portions (526) via bridge portion (528), this need not be so. Indeed, eye portion (524) may be connected to splint (522) via the fluid passageway region described in more detail below, or the flexible members described briefly above.

Figure 5G:
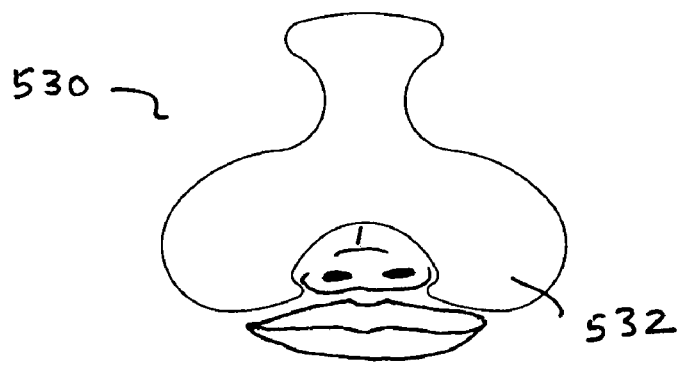
Figure 5H:
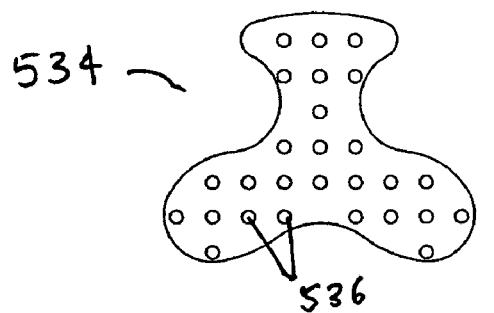
Figure 5I:
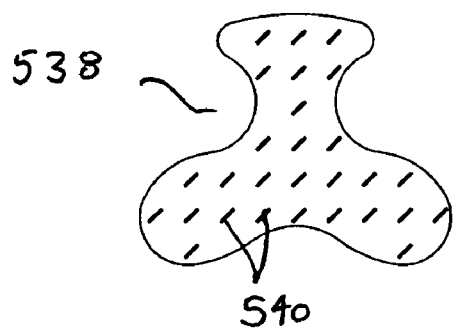

FIG. 5G depicts a similar variation to FIG. 5F, however here, the splint (530) comprises a base member (532) that has been extended down to the area immediately above the upper lip. FIGS. 5H and 5I show splints (534) and (538) respectively wherein the splints have perforations (536) and (540) therethrough. The perforations may be of any shapes (common geometric or otherwise), e.g., the circular perforations (536) depicted in FIG. 5H or the slit-like perforations (540) depicted in FIG. 5I, or the like. In addition, the perforations need not be uniformly distributed throughout the splint. Indeed the perforations may be randomly distributed throughout the splint, may have random geometries, and may have random sizes. Combinations of these random selections are also appropriate, although we note that is desirable that the perforations not be so large or so great in number so as to compromise the integrity of the splint.

As previously mentioned, these perforations may provide the device with a number of advantages. For example, in addition to reducing the overall weight of the device, these perforations may help provide better thermal conductivity to the splint. Furthermore, when a viscous liquid is utilized in combination with a splint having perforations therein, the perforations can allow expansion of the viscous liquid therein, and thus allow for give, or expansion of a swollen nose. Although, we note here that the viscous liquid need not penetrate or expand into the perforations. As with the viscous liquids described above, the viscous liquid of these variations may be made of any appropriate viscous material. The viscous liquid may also be covered or enveloped in a sterile material, but need not be. In addition, the viscous liquid may comprise at least one metallic fragment, e.g., in order to increase the thermal conductivity of the viscous liquid and the adjacent splint. The viscous liquid itself may also be made from a material having a high thermal conductivity.

Figure 6A:
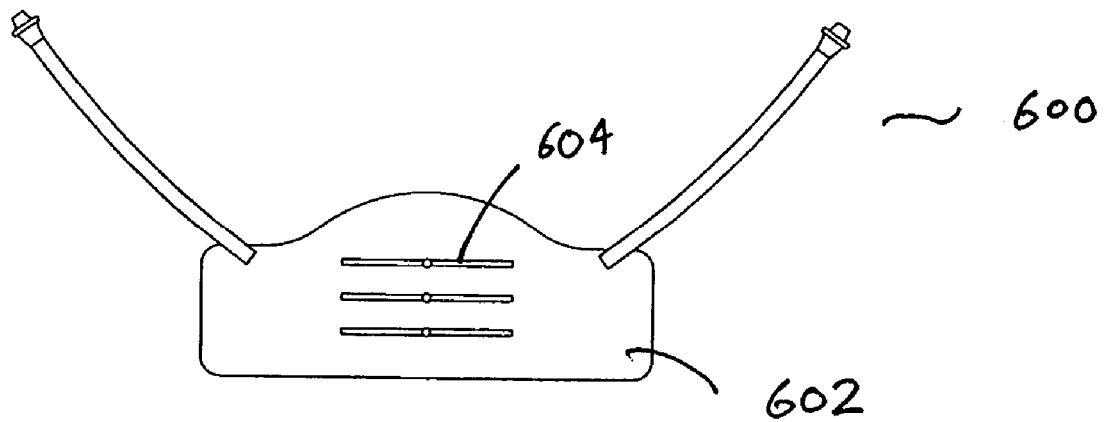
FIG. 6A depicts one example of a temperature-controllable device appropriate for use as described herein. Here, the device has not yet been molded to the contours of a subject's nose.
Figure 6B:
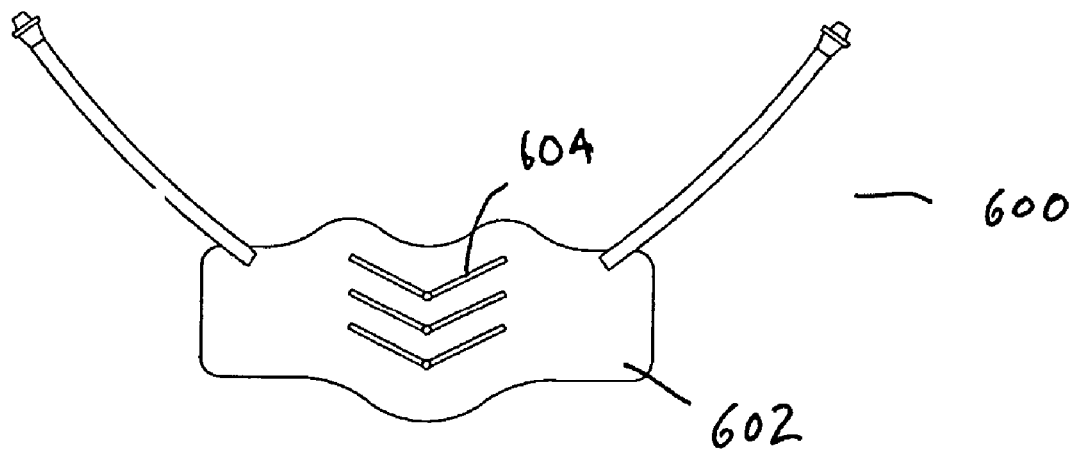
FIG. 6B shows the device of FIG. 6A after it has been molded to the contours of a subject's nose.

As shown by FIGS. 6A and 6B, the splint (600) may also have hinge regions (604) or the like, to aid in the molding of the splint to a subject (e.g., a subject's nose, as shown here). FIG. 6A depicts a splint (600) in a pre-molded configuration, while FIG. 6B depicts a splint configuration after it has been molded to the contours of a subject's nose. Also shown in FIGS. 6A and 6B are base portions (602), which as described above, can be designed with an extended length as desirable. While hinge regions are depicted in FIGS. 6A and 6B, it should be understood that hinge regions are not required. Indeed, the splint of the devices described herein may be made from any number of appropriate materials. For example, the splint may be made from aluminum, stainless steel, tin, any of the various plastics, any of the various alloys, waxes, rubbers, or mixtures thereof. So long as the splint is capable of stabilizing the particular injured area(s) being treated and is capable of providing adequate pressure thereto, there is no limit on the types of appropriate materials that may be used. Desirably, the splint is made from a non-toxic or biocompatible material. In addition, because the fluid passageway region may be adjacent to, or integral to the splint, as will be described in more detail below, it may be desirable that the splint be made of a material having a high thermal conductivity.

Figure 7A:
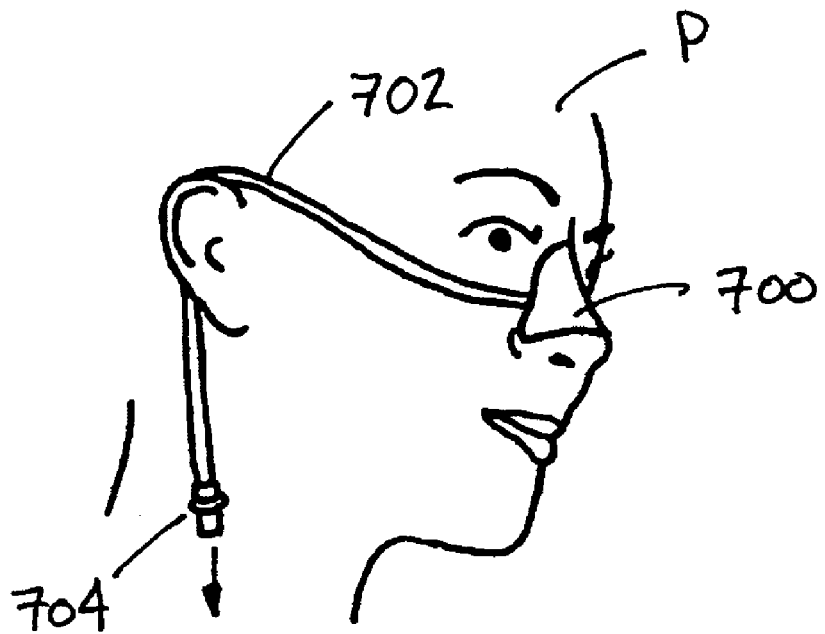
FIG. 7A shows one way in which the devices described herein may be used to treat a nose.

In general, the method of using the temperature-controllable devices to treat a nose comprises the steps of applying any of the temperature-controllable devices described herein to a nose of a subject in need thereof, and controlling the temperature of the device so as to provide a therapeutic benefit. For example, shown in FIG. 7A is subject (P) wearing device (700) for a therapeutic benefit. Subject (P) may have encountered a direct blow to the nose, for example, due to a sports injury or the like, or may have just undergone rhinoplasty or some similar such procedure. The subject (P) is shown wearing device (700) employing flexible member (702). Flexible member may be flexible tubing or the like. In addition, the device may be attached via a headband, using Velcro™, using clips, or using the adhesive portion described above, etc.

Figure 7B:
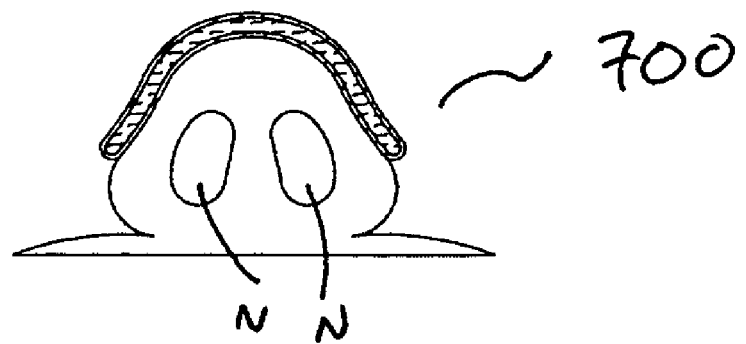
FIG. 7B shows an upward looking view of the device shown in FIG. 7A.

Outlet port (704), here shown as a quick disconnect is configured to attach to a fluid supply unit. The fluid supply unit functions to control the flow of the fluid through the fluid passageway region and has controls thereon to accurately and continuously control the temperature. In this fashion, the subject (P) may adjust the temperature of the fluid within the fluid passageway region to a range within his or her comfort level. In addition, the control of the fluid temperature will help prevent against overcooling of the injured area, which may also be problematic. FIG. 7B shows device (700) from FIG. 7A when viewed upwards. As shown there, the device (700) may have any of the configurations described herethroughout. Subject's (P) nostrils are indicated by the indicator (N).

Periorbital Temperature-Controllable Devices

The temperature-controllable devices described herein may also be configured as periorbital masks useful for applying temperature (e.g., cool or cold) therapy to the regions of the face, including the area around the eyes. FIGS. 8A and 8B show one variation of a periorbital mask. FIG. 8A illustrates the side of the device configured to contact the periorbital region of a subject's face. The device comprises a contact surface (801) which is shown as the outer surface of the fluid passageway region. This outer surface is shown as transparent, so that the inlet and outlet (805, 805') are visible, as well as the weld regions (810) within the fluid passageway region. The weld regions may serve as supports within the fluid passageway region, preventing regions of the passageway from collapsing when the device is worn, and pressure (e.g., from against the subject's face) is applied. The mask also has eye holes (820).

FIG. 8B shows the opposite side of the periorbital mask shown in FIG. 8A. The inlet and outlet (805, 805') project from the exterior side of the device, as shown. The outer surface of the mask comprises an opaque outer surface (830) that is flocked, so that a hook portion of a hook and latch fastener (such as Velcro™ hooks) may be attached to this outer surface. Thus, straps or other support structures may be attached to the outer surface, and may be used to hold the mask against a subject's periorbital region.

The device shown in FIGS. 8A and 8B may comprise a three (or more) layered structure, as previously described. FIG. 9 shows an exploded view of the mask shown in FIGS. 8A and 8B. In FIG. 9, there are three layers, corresponding to the contact portion layer (801), an inner layer (905), and the outer surface layer (830). The fluid passageway region is formed between the contact portion layer (801) and the inner layer (905). The edges of these two layers have been laminated together in a water-tight seal, to form a bladder region configured as the fluid passageway region. The inlet and outlet connectors (805, 805') are positioned between these two layers, and pass through the inner layer (905). The edges of the inlet and outlet connectors are laminated to the inner layer, permitting fluid to flow into and out of the fluid passageway region through the inlet and outlet ports. A second bladder region is formed by the lamination of the edges of the inner layer (905) and the outer surface layer (830). A splint (901) is placed between the inner layer (905) and the outer surface layer (830) prior to sealing the two regions. As described above, this pocket region may be sealed (as shown) or it may be open or openable, so that the splint may be removed or replaced. Any appropriate splint (or no splint) may be used. FIGS. 10A-10E show different splints that may be used with the periorbital device shown in FIGS. 8 and 9.

Figure 10A:
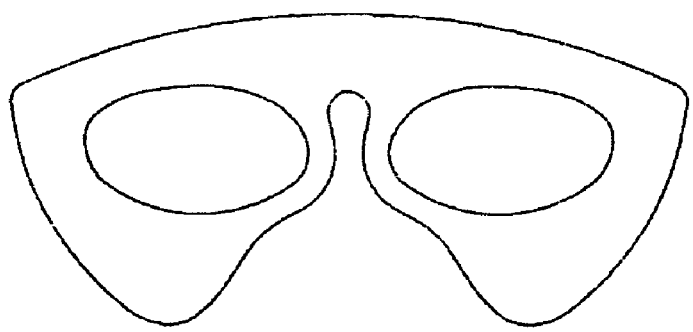
FIGS. 10A-10E show variants of splints that may be used in periorbital masks as shown in FIGS. 8 and 9.
Figure 10B:
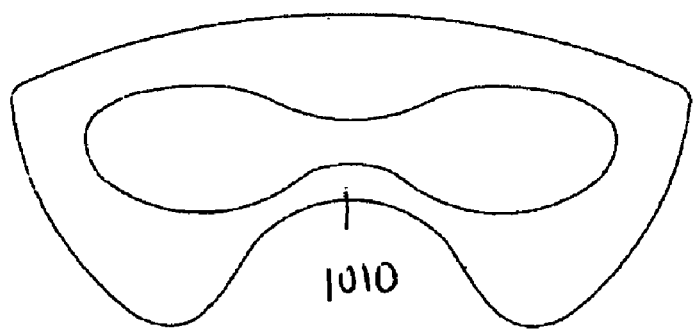
Figure 10C:
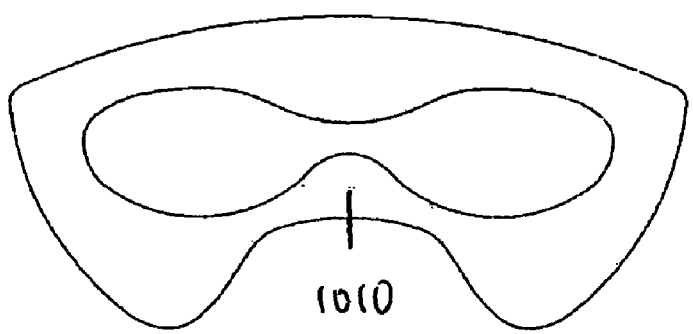

FIG. 10A shows a splint without any nose region, where the splint is substantially solid. This is the same splint as shown in FIGS. 8 and 9. As previously described, the splint may comprise a solid structure, or it may have holes or passages therethrough. The splints shown in FIGS. 10B and 10C include a nose region (1010) that may be molded over the subject's nose. In some variations of the periorbital mask, the splint may be comprised of a thermoplastic material that may be molded to fit a subject's periorbital region. Some of the splint materials useful for the devices described herein (including some of the thermoplastics) may be stiff but still somewhat flexible, even when set. Furthermore, some of the splint materials may change color or opacity to indicate when they are set or when they are moldable. A portion of the device (e.g., the outer layer or the contacting surface layer and the inner layer) may be transparent, as shown for FIGS. 8 and 9, providing visual clues about the status of the splint layer, as well as the status of the fluid passageway region, which may be visible.

Figure 10D:
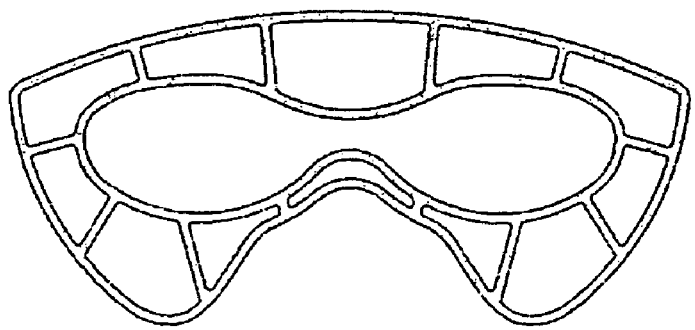
Figure 10E:
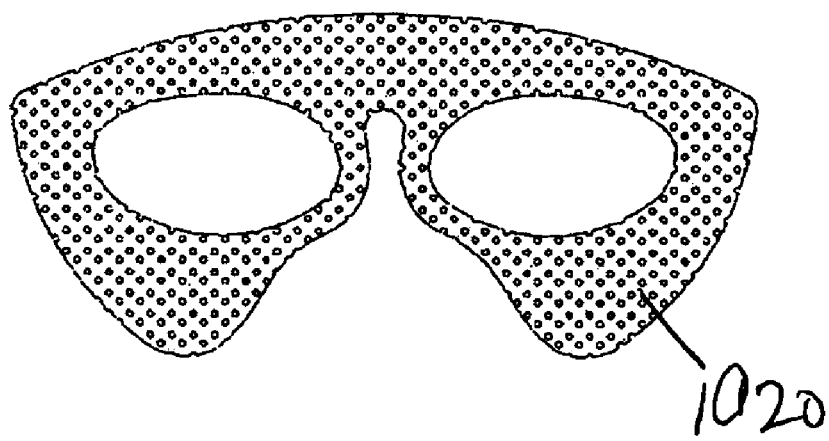

FIG. 10D shows a splint that is configured as a framework. This splint region may be lighter than the more substantial splints shown in FIGS. 10A-10C. Similarly, the splint shown in FIG. 10E includes perforations (1020), as described above. The temperature-controllable devices shown in FIGS. 8 and 9 have holes for a subject's eyes, through which a subject may see. In some variations, it may be desirable for the device to cover the eyes (or a larger portion of the eyes), as when a subject has a surgery on or around the eyelids. In FIG. 11, a mask having eye flaps (1150) is shown. FIG. 11 shows the outer surface region of a mask (1130); this outer surface may also be flocked as described for the mask in FIG. 8. The inner surface of the eye flaps facing a subject wearing the mask (not shown) may include a portion of the fluid passageway region. Thus, when the eye flaps are closed, the mask may provide temperature therapy to eye region of a subject wearing the mask. In FIG. 11, the eye flaps (1150) may be opened; a hook attachment site (1155) beneath each eye flap (1150) may be used to secure the flaps in the open position, since the outer surface of the eye flaps comprises a flocked (e.g., looped) material. Any appropriate attachment may be used (e.g., snaps, ties, etc.). In some variations, the eye flaps may be held closed by using any appropriate attachment.

Figure 12:
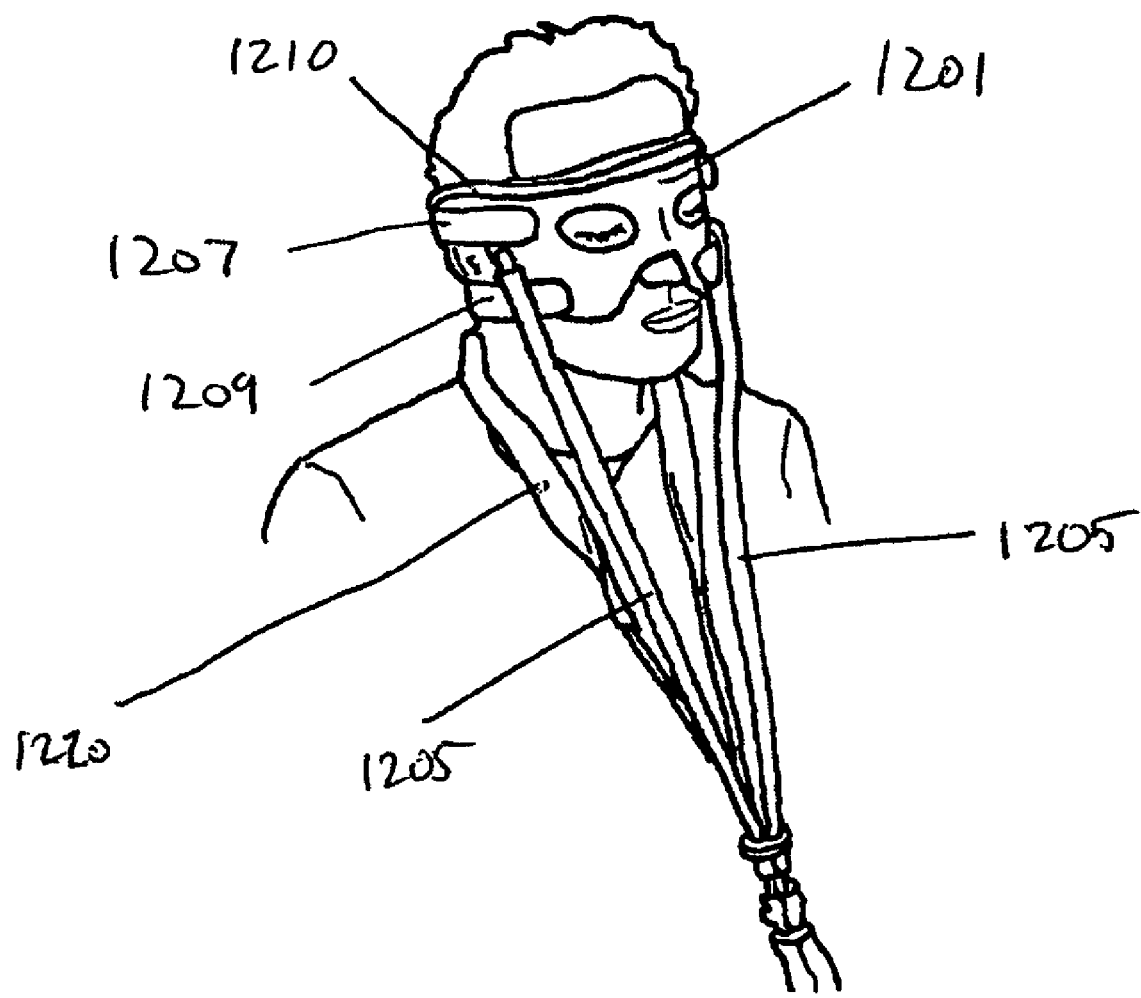
FIG. 12 shows a perspective view of a temperature-controllable device configured as a periorbital mask as it may be worn by a subject.

A periorbital mask (such as that shown in FIGS. 8 and 11) may be worn by a subject as shown in FIG. 12. The inlet and outlet of the periorbital mask (1201) are attached to tubing (1205) that is surrounded by an insulating layer. This tubing may connect to a fluid supply unit (not shown) that pumps temperature-controllable fluid (e.g., water) into and out of the mask (1201). The mask is secured onto the subject's face by an upper strap (1207), a lower strap (1209), and a headgear (1210). The headgear is shown as a flexible member that may be bent to conform to attach to the mask (1201) and the subject's head, and further may be bent around the subject's ears. The straps (1207, 1209), attach to the mask and may be adjustable to wrap behind the head to secure both sides of the mask over the periorbital region. These straps may also be elastic. As previously described, the outer surface of the mask (1201) may be flocked to permit attachment by a hook portion on the straps (1207, 1209) and the headgear (1210).

Finally, FIG. 12 also shows a neck strap (1220) used to help support and secure the attachment tubes (1205) connecting the inlet and outlet of the mask (1201) to the fluid source unit.

Thus, the subject's neck and the neck strap may support the weight of the connecting tubes, and therefore help stabilize the mask.

The periorbital masks described herein are merely illustrative of the kinds of temperature-controllable devices described herein. Other suitable temperature-controllable devices include devices covering the full face, or other regions of the face (e.g., chin, ears, cheeks, forehead, etc.), and other regions of the anatomy, such as the breast and abdomen. For example, a temperature-controllable device may be used following liposuction. Childbirth (e.g., vaginal childbirth or cesarean section) is another application that may benefit from a temperature-controllable device.

Vaginal Temperature-Controllable Devices

Figure 13A:
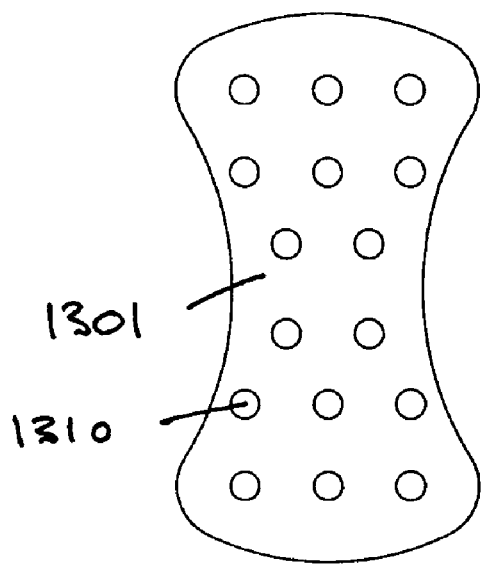
FIG. 13A is a perspective view of a temperature-controllable device configured as a feminine pad, as described herein.
Figure 13B:
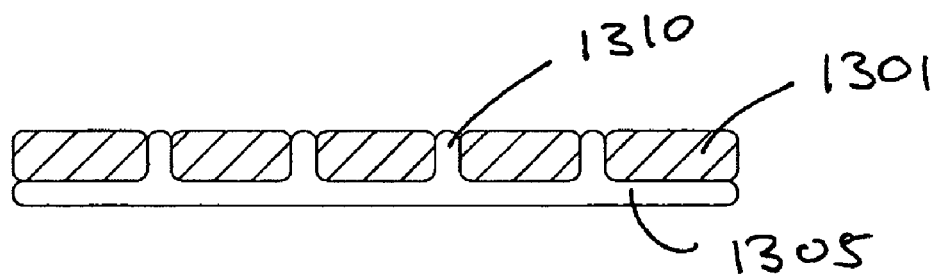
FIGS. 13B and 13C show sections through temperature-controllable devices configured as feminine pads, similar to that shown in FIG. 13A.

As briefly described above, a temperature-controllable device may also be used in the groin area. In particular, a temperature-controllable device may be used after childbirth or surgery. In some variations, the device comprises a fluid passageway region that intercalates with an absorbent pad, as previously described. FIG. 13A shows one example of a temperature-controllable device configured as a feminine pad. The device comprises an absorbent pad (1301) which secures over a fluid passageway region (1305). The fluid passageway region (1305) comprises a number of dimples or plugs (1310) which extend from the fluid passageway region and pass through corresponding holes in the absorbent pad (1301), as seen in the cross-section shown in FIG. 13B. These dimples (1310) may contact the subject to transfer heat between the subject and the device (e.g., for cooling). Furthermore, the dimples (1310) may also help secure the absorbent pad (1301) in position on the body-contacting surface of the device. In addition to the dimples, any other appropriate fastener (or fasteners) may be used, such as an adhesive, etc.

Figure 13C:
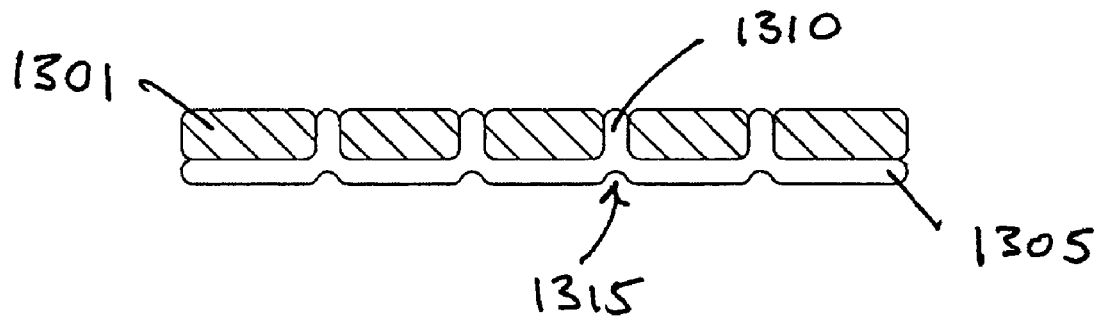

FIG. 13C shows a cross-section of another variation of the device shown in FIG. 13A, in which the fluid passageway comprises indentations (e.g., creases) on one side (1315). The creases may help make the device more flexible, enhancing the ability of the pad to fit the contour of the body.

Full Facial Devices and Multiple Connected Devices

FIG. 14A shows a perspective view of a variation of a temperature-controllable device in which the temperature-controllable device is configured as a full face mask (1401). In FIG. 14A, the full face mask is shown worn by a subject, and the mask is supported by a support structure (1405) worn over the subject's head, as previously described. The support structure 1405 in FIG. 14A is a head covering that partially covers the neck and head regions of the subject. This support structure (1405) includes attachments to secure the full face mask (1401) in position. For example, the attachments may comprise buttons, snaps, belts, etc. In one version, the head covering has region (e.g., surrounding the face opening) that has hooks (e.g., VELCRO™ hooks) to which a hook region (e.g., a flocked region) on the underside of the mask may attach. Arrows drawn on the mask illustrate possible fluid paths within the fluid passageway region.

FIG. 14B shows another view of the full face mask (1401) shown in FIG. 14A. The face mask (1401) has eye holes (1408), and an opening for the mouth and nose. The mask may conform the surface of the face (and may include splint regions, including moldable splint regions). Thus, the forehead region and the chin region of the mask are shown as regions that may be adjusted to fit the planes of the face. In some versions, regions of the mask maybe configured to overlap (e.g., the chin and forehead regions) to permit the mask to completely cover these regions of the face, and to be used by a variety of differently-sized subjects.

Figure 15A:
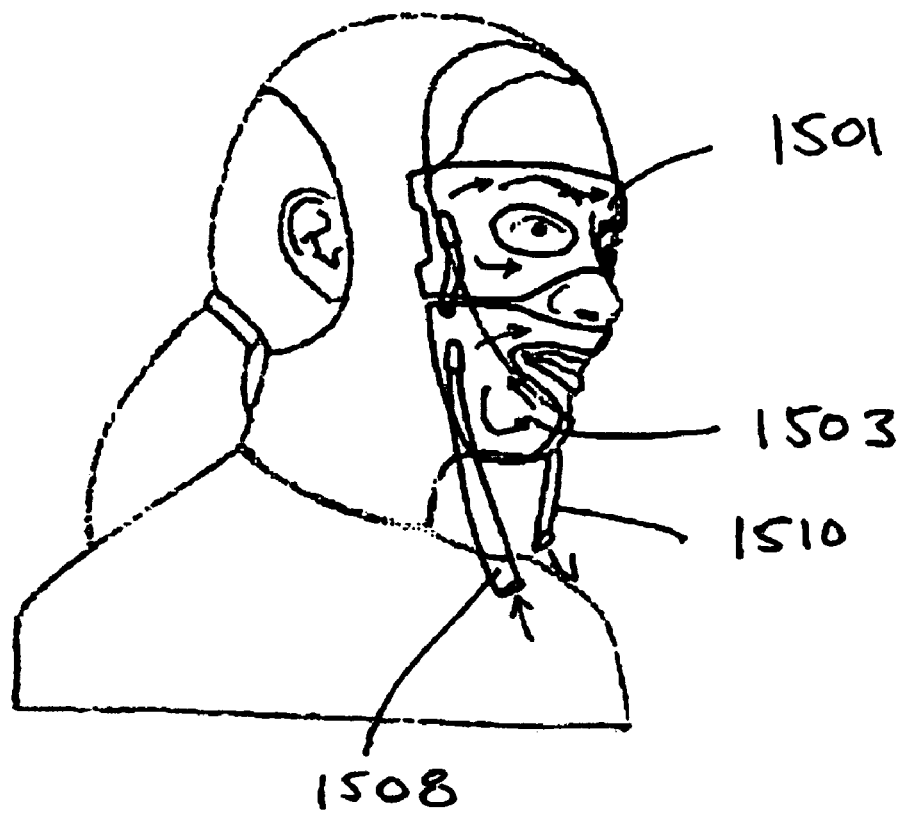
FIGS. 15A and 15B show two temperature-controllable devices connected together and to a single fluid supply unit.

A temperature-controllable device may comprise different regions, and may be connected in series (or in parallel) from one or more fluid source units. FIG. 15A shows a perspective view of another variation of a temperature-controllable device configured to fit over a subject's face, having two regions, a periorbital face mask (1501) and a full face add-on (1503). The two regions are connected to each other so that the fluid passageway region from both form a single fluid passageway region that is connected to a single fluid supply unit, as shown. One inlet (1508) and one outlet (1510) connect to the fluid supply unit. As in FIG. 14, the temperature-controllable device is connected to the user via a garment-type (e.g., a head covering) support structure.

Figure 15B:
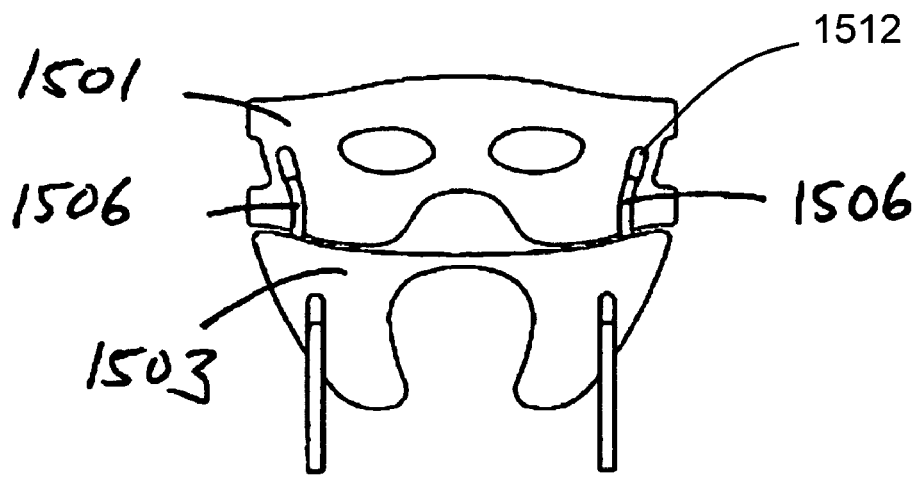

FIG. 15B shows the two-piece temperature-controllable device shown in FIG. 15A. As previously mentioned, a temperature-controllable device may comprise multiple temperature-controllable devices connected together. These connections may be temporary (e.g., they may be unhooked by the subject), or they may be permanent. In F*ig*. 15B, the pieces of the two-piece temperature controllable devices are shown permanently connected together through tubing (1506), and valve (1512) on either side of the mask (in some versions, a single connection may be used, or more than two connections). For example, the tubing connecting the pieces may be rf-welded to each piece.

Figure 16A:
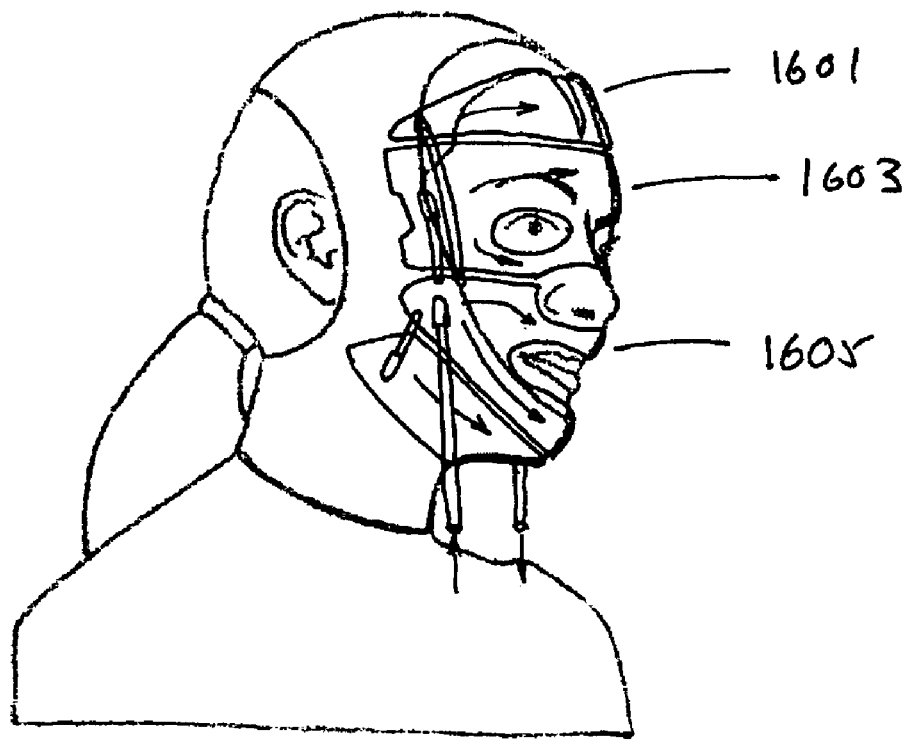
FIGS. 16A and 16B show three temperature-controllable devices connected together and to a single fluid supply unit.
Figure 16B:
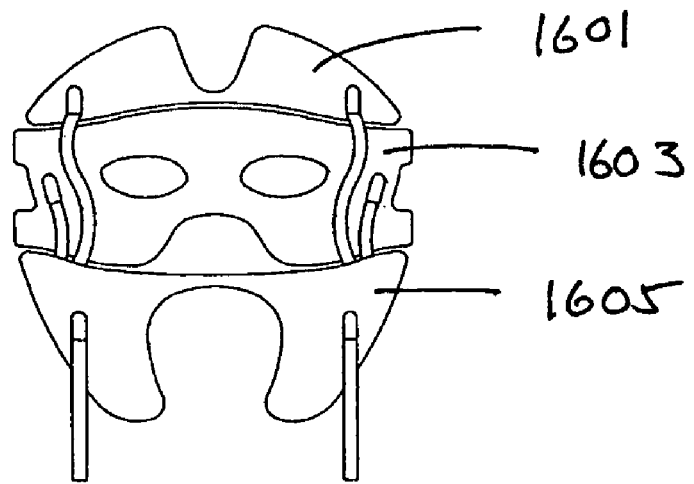

More than two pieces may be connected together to form a temperature-controllable device. For example, FIG. 16A and 16B show a three-piece temperature-controllable device, configured as a full face mask. This variation of the full face mask comprises a forehead pad (1601), a periorbital pad (1603), and a full-face add-on (1605). As shown in FIG. 16B, the fluid passageway regions of the three components of the full face mask are connected (shown as connected by tubing). The temperature-controllable device may comprise any appropriate number of regions. FIG. 17 shows a four-piece temperature controllable device comprising a forehead pad (1701), a periorbital pad (1703), a cheek pad (1705) and a neck pad (1707).

As has been demonstrated, the devices, methods, and kits described herein provide improved therapy to an injured area. However, it should be understood that the devices, methods, and kits described herein are not limited to the precise examples or advantages herein set forth. Accordingly, modifications of the above-described devices, methods, and kits, which are apparent to those of skill in the art, are intended to be within the scope of the appended claims.

What we claim is:

1. A temperature-controllable device for providing thermal therapy to a subject's face, said device comprising:
    a) a face mask, wherein said face mask comprises one or more regions, wherein said regions of said face mask are fluidically interconnected, and wherein said face mask has two openings for a subject's eyes;
    (b) a pliable fluid passageway for allowing a fluid to flow in each of said regions and between said interconnected regions;
    (c) a re-formable splint for applying pressure, wherein said splint is moldable to at least a portion of the subject's face, wherein said splint comprises a solid material, and wherein said solid material comprises:
        (i) a metal;
        (ii) a ceramic;
        (iii) a thermoplastic material; or
        (iv) any combination thereof; and
    wherein the splint is connected to the fluid passageway.

2. The device of claim 1, wherein the splint is releasably connected to the fluid passageway.

3. The device of claim 2, wherein the splint is releasably connected by a fastener selected from the group consisting of hook and loop fasteners, adhesives, snaps, rivets, buttons, zippers, magnets, and friction fittings.

4. The device of claim 1, further comprising multiple splints.

5. The device of claim 1, wherein the fluid passageway region is made at least in part from a material selected from the group consisting of vinyl, polyvinyl chloride, rubber, urethane, polyurethane, neoprene, silicone, and mixtures thereof.

6. The device of claim 1, wherein the fluid passageway permits pulsatile fluid flow.

7. The device of claim 6, further comprising a valve between at least two of said interconnected regions, wherein said valve is for creating a pressure differential in said fluid passageway between said interconnected regions, and wherein said pressure differential causes a pulsatile fluid flow.

8. The device of claim 1, wherein the fluid is blocked from at least one of said interconnected regions of said face mask.

9. The device of claim 1, further comprising one or more valves, wherein one of said valves is located between two of said interconnected regions of said face mask, wherein said valves are for controlling fluid flow into and out of at least one of said interconnected regions.

10. The device of claim 9, wherein at least one of said valves between two of said interconnected regions of said face mask comprises a temperature sensitive valve, wherein said temperature sensitive valve controls fluid flow between said two interconnected regions based on the temperature.

11. The device of claim 1, wherein the fluid passageway has a non-uniform thickness corresponding to a region of the subject's face.

12. The device of claim 1, further comprising an eye flap for each of said two eye openings, wherein said eye flaps can be in an open position or a closed position, and wherein said fluid passageway extends into said eye flaps.

13. The device of claim 1, further comprising an adhesive.

14. The device of claim 1, further comprising an inlet and an outlet, wherein both the inlet and the outlet are configured to attach to a fluid supply unit and to the fluid passageway.

15. The device of claim 14, further comprising an attachment region for connecting to at least one strap for securing the device to the subject's face.

16. The device of claim 1, further comprising an active agent, wherein the active agent is selected from the group consisting of a moisturizer, a surfactant, a disinfectant, an alcohol-based product, a cosmetic, a vitamin, an acid, a base, a pharmaceutical, and an anesthetic.

17. The device of claim 1, further comprising at least three layers, wherein at least two of said layers are bonded together to form at least part of said fluid passageway, wherein said bonded layers are pliable and fluid-resistant, wherein said third layer is at least partially bonded to one of said other layers, and wherein said splint is held between said third layer and one of said other layers.

18. The device of claim 1, further comprising a counter-current exchange pathway in said fluid passageway.

19. The device of claim 1, wherein said fluid passageway has an outer surface, wherein said outer surface is in contact with the subject's face, and wherein said outer surface is textured.

20. The device of claim 1, wherein said fluid has a high viscosity, a high thermal conductivity, or a high viscosity and a high thermal conductivity.

21. The device of claim 1, wherein said splint comprises perforations, wherein said perforations allow said splint to be deformable.

22. The device of claim 1, wherein said splint has a textured surface.

23. The device of claim 1, wherein said solid material of said splint comprises a metal, and wherein said metal is selected from the group consisting of aluminum, stainless steel, tin, and metal alloys.

24. The device of claim 1, wherein said splint is re-formable by heat activation, wherein heat activation of said splint comprises heating said splint to an activation temperature range, changing the shape of said splint, and lowering said splint below said activation temperature range.

25. The device of claim 1, further comprising a support structure, wherein said support structure is wearable over a subject's head, and wherein said face mask is supported by said support structure.

26. The device of claim 1, wherein one of said interconnected regions comprises a periorbital face mask, and wherein another of said interconnected regions comprises a full face add on, and wherein said periorbital face mask and said full face add on are fluidically connected.

* * * * *